United States Patent
Giannini et al.

(10) Patent No.: US 9,302,998 B2
(45) Date of Patent: Apr. 5, 2016

(54) ARYL TRIAZOLE COMPOUNDS WITH ANTITUMOURAL ACTIVITY

(75) Inventors: Giuseppe Giannini, Pomezia (IT); Walter Cabri, Rozzano (IT); Loredana Vesci, Rome (IT); Maria Luisa Cervoni, Pomezia (IT); Claudio Pisano, Aprila (IT); Maurizio Taddei, Monteriggioni (IT); Serena Ferrini, Gracciano di Colle Val d'Elsa (IT)

(73) Assignee: SIGMA-TAU RESEARCH SWITZERLAND S.A., Mendrisio (CH)

( * ) Notice: Subject to any disclaimer, the term of this patent is extended or adjusted under 35 U.S.C. 154(b) by 34 days.

(21) Appl. No.: 13/996,359

(22) PCT Filed: Dec. 13, 2011

(86) PCT No.: PCT/EP2011/072558
§ 371 (c)(1),
(2), (4) Date: Apr. 23, 2014

(87) PCT Pub. No.: WO2012/084602
PCT Pub. Date: Jun. 28, 2012

(65) Prior Publication Data
US 2014/0329812 A1 Nov. 6, 2014

(30) Foreign Application Priority Data
Dec. 20, 2010 (EP) .................... 10195949

(51) Int. Cl.
C07D 413/12 (2006.01)
C07D 401/10 (2006.01)
C07D 403/10 (2006.01)
C07D 249/06 (2006.01)

(52) U.S. Cl.
CPC ............ C07D 249/06 (2013.01); C07D 401/10 (2013.01); C07D 403/10 (2013.01); C07D 413/12 (2013.01)

(58) Field of Classification Search
CPC ... C07D 413/12; C07D 401/10; C07D 403/10
See application file for complete search history.

(56) References Cited

U.S. PATENT DOCUMENTS

2006/0235058 A1 10/2006 Cheung et al.
2010/0113447 A1 5/2010 Burlison et al.

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
International Search Report in counterpart PCT/EP2011/072558.

* cited by examiner

Primary Examiner — Shawquia Jackson
(74) Attorney, Agent, or Firm — Lucas & Mercanti, LLP.

(57) ABSTRACT

The present invention relates to aryl triazole derivatives of Formula I having antitumoural activity through, as one possible biological target, the molecular chaperone heat shock protein 90 (Hsp90) inhibition. The invention includes the use of such compounds in medicine, in relation to cancer disease as well as other diseases where an inhibition of Hsp90 is responsive, and the pharmaceutical composition containing such compounds.

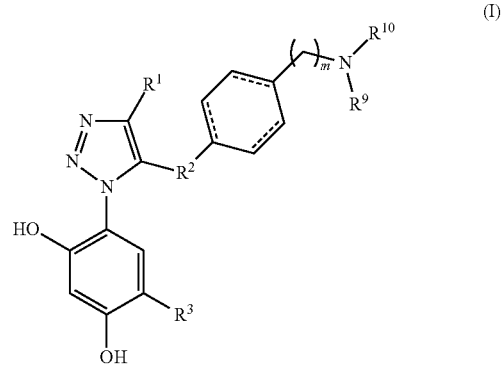

8 Claims, No Drawings

ARYL TRIAZOLE COMPOUNDS WITH ANTITUMOURAL ACTIVITY

This application is a U.S. national stage of PCT/EP2011/072558 filed on Dec. 13, 2011, which claims priority to and the benefit of European Application No. 10195949.2, filed on Dec. 20, 2010, the contents of each of which are incorporated herein by reference.

FIELD OF THE INVENTION

The present invention relates to aryl triazole derivatives having antitumoural activity through, as one possible biological target, the molecular chaperone heat shock protein 90 (Hsp90) inhibition. The invention includes the use of such compounds in medicine, in relation to cancer diseases as well as neurodegenerative diseases, inflammatory diseases, autoimmune diseases, cerebral ischemia or parasitemia including malaria, where an inhibition of Hsp90 is responsive, and the pharmaceutical composition containing such compounds.

BACKGROUND OF THE INVENTION

Heat shock proteins (Hsp's) play a key role in cell protection against various cell stress factors (i.e. toxic xenobiotic, chemotherapy, radiation) acting as a protective factor against the misfolding of essential proteins involved in maintaining cell functionality. Hsp90 proteins, members of these molecular chaperones are proteins that play a key role in the conformational maturation, stability and function of so-called "client" proteins, many of them belonging to the oncogenic protein family, such as Bcr-Abl, p53, Raf-1, Akt, ErbB2, EGFR, Hif and other proteins, as well as steroid hormone receptors. The inhibition of Hsp90 triggers the disruption of the Hsp90-client protein complex, and subsequently, its proteasome-mediated degradation causes loss of function and inhibition of cell growth. Interestingly, heat shock protein 90 has emerged as an important target in several diseases. In particular, the role played by Hsp90 in regulating and maintaining the transformed phenotype in cancers and neurodegenerative diseases has been recently identified, as well as its roles in fungal and viral infections (Solit D. B., et al., *Drug Discov. Today,* 2008, 13 (1-2), 38). In particular, Hsp90 inhibition has also been reported to be beneficial in the treatment of neurodegenerative diseases such as dementia with Lewy bodies, amyotrophic lateral sclerosis, spinal and bulbar muscular atrophy, spinocerebellar ataxias, Parkinson, Huntington and Alzheimer's diseases (Taylor D. M., et al., Cell Stress Chaperones, 2007, 12, 2, 151; Yang Z., et al., *Nat. Med.,* 2007, 13, 3, 348; Katsuno M., et al., *Proc. Natl. Acad. Sci. USA,* 2005, 102, 46, 16801; Gallo K. A., *Chem. Biol.,* 2006, 13, 115; Luo W., et al., *Proc. Natl. Acad. Sci.,* 2007, 104, 9511; Macario A. J., et al., *N. Engl. J. Med.,* 2005, 353, 1489; Dou F., et al., *Int. J. Mol. Sci.,* 2007, 8, 51); inflammatory diseases (Vega V. L., et al., *Mol. Biol. Cell.,* 2003, 14, 764; Poulaki V., et al., *Faseb J.,* 2007, 21, 2113); cerebral ischemia (Lu A., et al., *J. Neurochem.,* 2002, 81, 2, 355) and malaria (Kumar R., et al., *J. Biosci.,* 2007, 32, 3, 531).

Moreover, many Hsp90 client proteins are over-expressed in cancer, often in mutated forms, and are responsible for unrestricted cancer cell proliferation and survival. Interestingly, Hsp90 derived from tumour cells has particularly high ATPase activity with higher binding affinity to Hsp90 inhibitors than the latent form in normal cells, allowing specific targeting of Hsp90 inhibitors to tumour cells with little inhibition of Hsp90 function in normal cells (Chiosis G., et al., *ACS Chem. Biol.,* 2006, 1, 5, 279). In addition, Hsp90 has also been recently identified as an important extracellular mediator for tumour invasion (Eustace B. K., et al., *Nature Cell Biol.,* 2004, 6, 6, 507; Koga F., et al., Cell cycle, 2007, 6, 1393).

Thus, Hsp90 is considered a major therapeutic target for anticancer drug development because inhibition of a single target represents attack on all of the hallmark traits of cancer.

Since the discovery that two natural compounds, geldanamycin and radicicol, were able to inhibit Hsp90 function through binding to an ATP binding pocket in its N-terminal domain, the interest for Hsp90 inhibitors has grown. The natural antibiotic geldanamycin was shown to exhibit potent antitumour activity against human cancer cells (Whitesell L., et al., Cancer Res., 1992, 52, 1721), but significant toxicity prevented its clinical development (Supko J. G., et al., *Cancer Chemother. Pharmacol.,* 1995, 36, 305).

The first-in-class Hsp90 inhibitor to enter clinical trials was the geldanamycin analogue 17-AAG (i.e., 17-allylaminogeldanamycin). Even though high in vitro activity characterizes this geldanamycin derivative, its interest is shadowed by poor solubility coupled to hepatotoxicity properties (Jez J. M., et al., *Chem. Biol.,* 2003, 10, 4, 361). All clinical trials involving this compound have been halted in July 2010. Some of these above mentioned problems had been partially solved by the discovery of 17-dimethylaminoethylgeldanamycin, however all clinical development was halted because of unfavourable toxicity. Radicicol, a natural macrocyclic antifungal antibiotic, was found to inhibit Hsp90 protein by interacting at a different site of action than Geldanamycin (Sharma S. V., et al., *Oncogene,* 1998, 16, 2639). However, due to its intrinsic chemical instability it was deprived of in vivo activity.

Another important class of inhibitors resides in the purine scaffold. This class of derivatives was devised by structural homology with ATP. Among the many inhibitors developed within this family, PU24FC1 and BIIB021 were found to possess high in vitro and in vivo activity (He H., et al., *J. Med. Chem.,* 2006, 49, 381; Lundgren K., et al., *Mol. Cancer. Ther.,* 2009, 8, 4, 921).

High-throughput screening campaigns permitted the discovery of benzisoxazole derivatives endowed of Hsp90 inhibitory properties having a resorcinol moiety in position 3 (Gopalsamy A., et al., *J. Med. Chem.,* 2008, 51,373).

Various other classes of Hsp90 inhibitors have been disclosed such as, 4,5-diarylpyrazoles (Cheung K. M., et al., *Bioorg. Med. Chem. Lett.,* 2005, 15, 3338); 3-aryl, 4-carboxamide pyrazoles (Brough P. A., et al, *Bioorg. Med. Chem. Lett.,* 2005, 15, 5197); 4,5-diarylisoxazoles (Brough P. A., et al., *J. Med. Chem.,* 2008, 51, 196); 3,4-diaryl pyrazole resorcinol derivative (Dymock B. W., et al., *J. Med. Chem.,* 2005, 48, 4212; Smith N. F., et al., *Mol. Cancer. Ther.,* 2006, 5, 6, 1628); thieno[2,3-d]pyrimicline (WO2005034950, AACR 2009, Denver, Colo., poster 4684). Further heterocyclic derivatives containing three heteroatoms have also been described as possessing Hsp90 inhibitory properties. WO2009134110 disclosed 4,5-cliaryl thiadiazoles which demonstrated good Hsp90 binding affinity, but somehow rather modest cell growth inhibition. Another class of aza-heterocyclic adducts, namely triazole derivatives, has been disclosed abundantly. Indeed, within the triazole family of compounds, the 1,2,4-triazole scaffold has been profusely documented as possessing Hsp90 inhibiting properties. WO2009139916 (Synta Pharmaceuticals Corp.) disclosed tricyclic 1,2,4-triazole derivatives inhibiting Hsp90 at high micromolar concentrations. The same company later filed almost contemporaneously two further patent applications disclosing trisubstituted 1,2,4-triazole derivatives whose general formulae were partially overlapping and both covering a very large chemical space (WO10017479 and WO10017545). Within the first application the compounds are expected, to the say of the Applicant, to be endowed of numerous biological properties, but said expectation is not confirmed by any promising biological activity. Indeed, all reported biological data but one refer to a Hsp90 $IC_{50}$ greater than 10 μM. Promising biological activity is however reported within WO10017545. Few days ago, Synta Pharmaceuticals Corp. Reported about an unique triazolone-containing Hsp90 inhibitor named ganetespib (previously referred as to STA-9090, or as its highly soluble phosphate prodrug STA-1474) potentially having broad application for a variety of human malignancies. This compound was claimed in WO06055760.

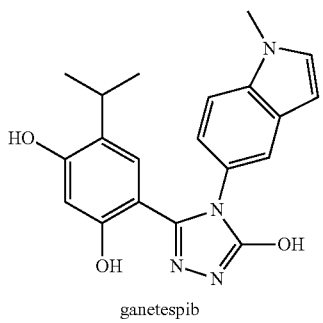 [SMILES: CC(C)c1cc(-c2nnc(O)n2-c2ccc3c(ccn3C)c2)c(O)cc1O]

ganetespib

Interestingly, 1,2,3-triazole analogues have not been studied as much as the 1,2,4 regioisomers. A myriad of heterocyclic derivatives, among which 1,2,3-triazole compounds can be found, are encompassed within WO05000300 even though only three are specifically disclosed. U.S. Pat. No. 7,728,016 patent, based on the previous application, claims 1,2,3-triazole compounds, although only one of the three specifically disclosed 1,2,3-triazole was alleged to possess a Hsp90 $IC_{50}$<10 μM. None of these derivatives are encompassed within the present application. However, meanwhile lots of Hsp90 inhibitors among the literature have demonstrated to possess nanomolar activity, no real teaching can be gathered from such patent since the biological data is expressed using a scale that does not allow one skilled in the art of heat shock protein to appreciate the true biological activity of this sole derivative. Therefore, example 3 of patent application U.S. Pat. No. 7,728,016 was synthesized and tested in house to assess its affinity toward the biological target and its cytotoxic property. Both were found to be rather modest being greater than 10 μM (i.e., binding affinity) and greater than 1 μM (i.e., cytotoxic activity). In the cytotoxic assay, 1 μM was the maximum concentration tested.

No Hsp90 inhibitor has yet made it through clinical trials and been approved by the Food and Drug Administration as a cancer treatment either for stability, toxicity or efficacy issues.

Therefore, the desire of potent and selective Hsp90 inhibitors remains an interesting and promising goal.

We have now found that 1,4,5-trisubstituted and 1,5-disubstituted 1,2,3-triazole derivatives are endowed of high and unexpected Hsp90 inhibitory properties. 1,2,3-triazole derivatives, structurally different (but with a certain degree of similarity) from the ones of the present invention, and possessing unrelated biological properties are known.

U.S. Pat. No. 7,803,822 patent discloses 1,2,3-triazole derivatives of formula 1 as thrombin receptor antagonists.

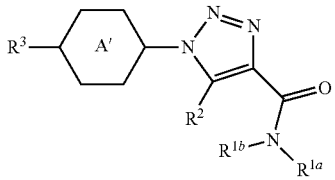

Formula 1

DE 10315570 discloses aryltriazoles of formula 2 as glycine transporter inhibitors.

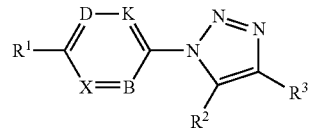

Formula 2

Biaggi G., et al. reported lately 1,5-cliarylsubstituted 1,2,3-triazoles as potassium channel activators (Biaggi G., et al., Il Farmaco, 2004, 59, 5, 397). Glaxo Group Ltd. also reported mGluR5 receptor antagonists possessing the 1,2,3-triazole amide unit, as useful for treating psychotic disorders (WO2009115486).

DESCRIPTION OF THE INVENTION

The present invention relates to a new class of 1,4,5-trisubstituted and 1,5-disubstituted 1,2,3-triazole compounds and its use as Hsp90 inhibitors. A core 1,2,3-triazole ring with an aromatic substitution on position 1, and a structurally limited substitution on position 5 containing a six-membered substituted carbocycle are the principle characterising features of the compounds of the present invention.

The invention provides compounds of formula (I) or a salt, N-oxide, hydrate or solvate thereof. It also further provides the use of compounds of formula (I) or a salt, N-oxide, hydrate or solvate thereof for the preparation of a composition for inhibition of Hsp90 activity.

The invention comprises compounds of general formula I

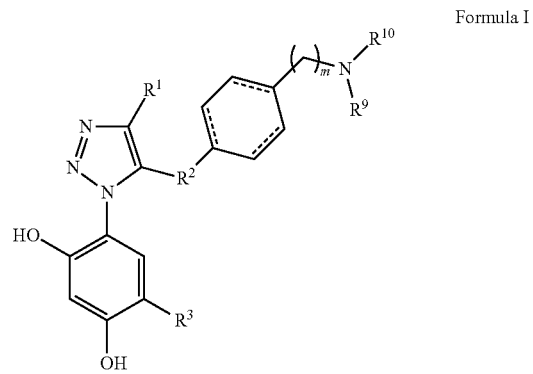

Formula I wherein,
$R^1$ is H, $CONR^4R^5$;
$R^5$ is H, $(C_1-C_6)$-alkyl or $(C_3-C_{10})$-cycloalkyl each being optionally substituted once or more with OH, OMe, Cl, F;
$R^4$ is H, $(C_1-C_4)$-alkyl or $CH(R^{11})COR^{12}$; or
$R^4$ and $R^5$ taken together with the nitrogen atom to which they are attached form a three to seven membered heterocycle optionally containing a further heteroatom selected from the group consisting of N, O or S; and wherein said heterocycle is optionally substituted once or more by OH, OMe, ($C_1$-$C_4$)-alkyl, optionally substituted phenyl, or benzyl;

$R^{11}$ is a side chain of a natural α-amino acid;
$R^{12}$ is OH, amino, alkylamino or dialkylamino;
$R^2$ is a bond, —NH(CO)—, —N($R^7$)— or —N($R^7$)$CH_2$—;
$R^7$ is H, ($C_1$-$C_4$)-alkyl or $CO_2R^8$;
$R^8$ is ($C_1$-$C_4$)-alkyl or benzyl; the endocyclic symbols $≡$ are, for each single compound, all double bonds or all single bonds;

m is an integer comprised between 0 and 3;

$R^9$ and $R^{10}$ are independently from each other ($C_1$-$C_4$)-alkyl optionally substituted with OH, cycloalkyl, heterocycloalkyl, OMe, amino, ($C_1$-$C_6$)-alkylamino or ($C_1$-$C_6$)-dialkylamino; heterocycloalkyl optionally substituted once or more by alkyl, amino, ($C_1$-$C_6$)-alkylamino or ($C_1$-$C_6$)-dialkylamino; cycloalkyl; or $R^9$ and $R^{10}$ taken together with the nitrogen atom to which they are attached form a heterocycle ring chosen from the group consisting of piperidyl, pyrrolidinyl, piperazinyl or morpholinyl, each of them being optionally substituted once or more by F, Cl, Br, OH, OMe, amino, ($C_1$-$C_6$)-alkylamino, ($C_1$-$C_6$)-dialkylamino, ($C_1$-$C_4$)-alkyl, hydroxyalkyl, optionally substituted phenyl, or benzyl; or an imidazole unsaturated heterocycle;

$R^3$ is Cl, Et or i-Pr;

their tautomers, their geometrical isomers, their optically active forms such as enantiomers, diastereomers and their racemate forms, as well as their pharmaceutically acceptable salts thereof.

The term "alkyl", unless otherwise specified, refers to linear or branched alkyl groups having from 1 to 20 carbon atoms, or preferably, 1 to 12 carbon atoms or even more preferably 1 to about 6 carbon atoms.

The term "($C_3$-$C_{10}$)-cycloalkyl" refers to a saturated or partially unsaturated (i.e., not aromatic) carbocyclic group of from 3 to 10 carbon atoms having a single ring or multiple condensed rings. Examples of ($C_3$-$C_{10}$)-cycloalkyl include cyclopropyl, cyclobutyl, cyclopentyl, cyclohexyl, norbornyl, adamantyl and the like.

The terms "heterocycloalkyl" and heterocycle refer to a saturated or partially unsaturated (i.e., not aromatic) four-, five-, six- or seven-membered ring containing one or two heteroatoms, which may be the same or different, selected from the group consisting of nitrogen, oxygen or sulfur atoms, and which ring may be substituted with amino or alkyl. Preferred heterocycloalkyl include azetidine, pyrrolidine, piperidine, piperazine, ketopiperazine, 2,5-diketopiperazine, morpholine and thiomorpholine.

The expression "optionally substituted" except when specified, generally refers to optional substituents selected from the group consisting of ($C_1$-$C_6$)-alkyl, OH, alkoxy, amino and aminocarbonyl.

The term "amino" refers to the group —$NH_2$.

The term "alkylamino" refers to the group —NHR where R is "alkyl" as defined above.

The term "dialkylamino" refers to the group —NRR' where R and R', being R and R' the same or different are "alkyl" as defined above.

The term "aminocarbonyl" refers to a carbonyl moiety substituted by an amino group as above defined.

The term "aryl" refers to an aromatic carbocyclic group of 6 to 14 carbon atoms having a single ring (e.g., phenyl) or multiple rings that may be attached in a pendent manner or may be fused. Preferred aryl include phenyl, naphthyl, phenantrenyl, biphenyl and the like. Said "aryl" may have 1 to 3 substituents chosen among hydroxyl, halogen, haloalkyl, cyano, ($C_1$-$C_6$)-alkyl, ($C_1$-$C_6$)-alkoxy, amino and ($C_1$-$C_6$)-aminoalkyl.

The term "heteroaryl" refers to an optionally substituted monocyclic heteroaromatic, or an optionally substituted bicyclic fused-ring heteroaromatic group. Particular examples of heteroaromatic groups include pyridyl, pyrrolyl, furyl, thienyl, imidazolyl, oxazolyl, isoxazolyl, thiazolyl, isothiazolyl, pyrazolyl, benzofuryl, [2,3-dihydro]-benzofuryl, isobenzofuryl, benzothienyl, benzotriazolyl, indolyl and isobenzothienyl.

The expression "side chain of a natural α-amino acid" refers to the side chain of any of the 20 natural amino acids, in all possible isomeric forms, wherein said α-amino acid is chosen among glycine, alanine, phenylalanine, valine, leucine, isoleucine, aspartic acid, asparagine, glutamic acid, glutamine, serine, lysine, histidine, methionine, proline, cysteine, threonine, tryptophan, arginine and tyrosine. For clarity purpose, and as for example, the side chains of alanine and valine are respectively methyl and isopropyl.

The expression "pharmaceutically acceptable salts" refers to salts of the below identified compounds of formulae (I), that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, toluene sulfonic acid, naphthalene clisulfonic acid, methanesulfonic acid and poly-galacturonic acid. When the salt is of a mono acid (for example, the hydrochloride, the hydrobromide, the p-toluenesulphonate, or the acetate), at least one molar equivalent and usually a molar excess of the acid is employed. However, when such salts as the sulphate, the hemisuccinate, the hydrogen phosphate, or the phosphate are desired, the appropriate and exact chemical equivalents of acid are generally used. Suitable pharmaceutically acceptable base addition salts for the compound of the present invention include metallic salts made from aluminium, calcium, lithium, magnesium, potassium, sodium and zinc or organic salts made from lysine, N,N'-clibenzylethylenecliamine, chloroprocaine, choline, diethanolamine, ethylenediamine, meglumine (N-methylglucamine) and procaine. Sodium salts are particularly preferred.

The invention furthermore provides a process for the preparation of compounds of formula I, which can be obtained as detailed underneath.

Compounds of general formula I wherein $R^1$ is —$CONR^4R^5$ and $R^2$ is a bond can be obtained by a process comprising the reaction of a compound of formula II

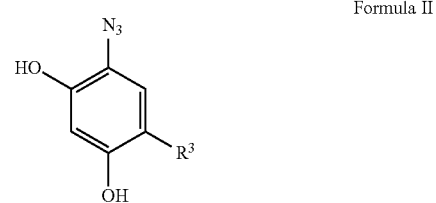

Formula II wherein $R^3$ is as previously defined, with a compound of formula III Formula III

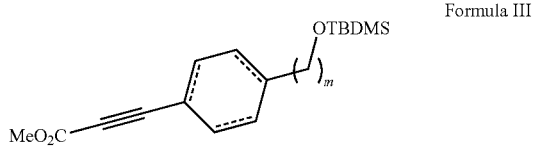

in a polar aprotic solvent such as DMF in neutral atmosphere in the presence of a ruthenium-based catalyst (e.g., [Cp*RuCl]4).

Compounds of general formula I wherein $R^1$ is $CONR^4R^5$, $R^2$ is $—N(R^7)—$ or $—N(R^7)CH_2—$, can be obtained by a process comprising the reaction of a compound of formula II as herein above defined, with a compound of formula IV Formula IV

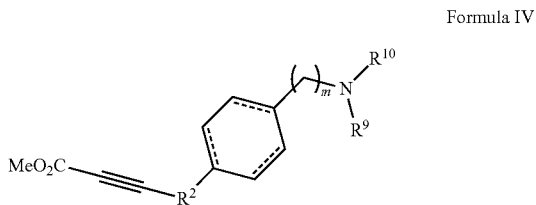

wherein $R^9$ and $R^{10}$ have the meaning defined for compounds of formula I and $R^2$ is $—N(R^7)—$ or $—N(R^7)CH_2—$, in a polar aprotic solvent such as DMF in neutral atmosphere in the presence of a ruthenium-based catalyst (e.g., [Cp*RuCl]4).

In all said transformations, any interfering reactive group can be protected and then deprotected according to well-established procedures described in organic chemistry (see for example: Greene T. W. and P. G. M. Wuts "Protective Groups in Organic Synthesis", J. Wiley & Sons, Inc., 3rd Ed., 1999) and well known to those skilled in the art.

All said transformations are only examples of well-established procedures described in organic chemistry (see for example: J. March "Advanced Organic Chemistry", J. Wiley & Sons, Inc., 4th Ed., 1992) and well known to those skilled in the art.

We have found that the derivatives of formula I and their pharmaceutically acceptable salts, prepared according to the invention, are useful agents for the treatment of disease states, disorders and pathological conditions mediated by Hsp90; in particular for the treatment of cancer diseases, neurodegenerative diseases, inflammatory diseases; cerebral ischemia and malaria.

The term "therapeutically effective amount" as used herein refers to an amount of a therapeutic agent needed to treat, ameliorate a targeted disease or condition, or to exhibit a detectable therapeutic effect.

The pharmaceutical compositions will contain at least one compound of Formula I as an active ingredient, in an amount such as to produce a significant therapeutic effect. The compositions covered by the present invention are entirely conventional and are obtained with methods which are common practice in the pharmaceutical industry, such as, for example, those illustrated in *Remington's Pharmaceutical Science Handbook*, Mack Pub. N.Y.—last edition. According to the administration route chosen, the compositions will be in solid or liquid form, suitable for oral, parenteral or intravenous administration. The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

For any compound, the therapeutically effective dose can be estimated initially either in cell culture assays or in animal models, usually mice, rats, guinea pigs, rabbits, dogs, or pigs.

The animal model may also be used to determine the appropriate concentration range and route of administration. Such information can then be used to determine useful doses and routes for administration in humans. In calculating the Human Equivalent Dose (HED) it is recommended to use the conversion table provided in Guidance for Industry and Reviewers document (2002, U.S. Food and Drug Administration, Rockville, Md., USA).

The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.001 mg/kg to 10 mg/kg, preferably 0.05 mg/kg to 50 mg/kg. Compositions may be administered individually to a patient or may be administered in combination with other agents, drugs or hormones.

The medicament may also contain a pharmaceutically acceptable carrier, for administration of the therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol.

Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal or rectal means.

The compositions for oral administration may take the form of bulk liquid solutions or suspensions, or bulk powders. More commonly, however, the compositions are presented in unit dosage forms to facilitate accurate dosing.

The expression "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include refilled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

Dosage treatment may be a single dose schedule or a multiple dose schedule.

A further object of the present invention are pharmaceutical compositions containing one or more of the compounds of formula I described earlier, in combination with excipients and/or pharmacologically acceptable diluents.

An even further object of the present invention regards said compounds of general formula I for use in the treatment of disorders where inhibition of Hsp90 would result in improving the health of the patient. In particular, patients suffering from cancer diseases, neurodegenerative diseases, inflammatory diseases, cerebral ischemia and malaria can be treated.

Preferred compounds are the ones selected from the group consisting of 4-isopropyl-6-[5-(4-(morpholin-4-ylmethyl-phenyl)-[1,2,3]-triazol-1-yl)benzene-1,3-diol; 4-{5-[4-(3-hydroxy-piperidin-1-ylmethyl)-phenyl]-[1,2,3]triazol-1-yl}-6-isopropyl-benzene-1,3-diol; 4-{5-[4-(4-benzyl-piperazin-1-ylmethyl)-phenyl]-[1,2,3]triazol-1-yl}-6-isopropyl-benzene-1,3-diol; 4-isopropyl-6-{5-[4-(4-phenyl-piperazin-1-ylmethyl)-phenyl]-[1,2,3]triazol-1-yl}-benzene-1,3-diol; 1-(2,4-dihydroxy-5-isopropyl-phenyl)-5-(4-morpholin-4-ylmethyl-phenyl)-1H-[1,2,3]triazole-4-carboxylic ethyl amide; (R,S)-1-(2,4-dihydroxy-5-isopropyl-phenyl)-5-[4-(3-hydroxy-piperidin-1-ylmethyl)-phenyl]-1H-[1,2,3]triazole-4-carboxylic acid ethylamide; 1-(2,4-dihydroxy-5-isopropyl-phenyl)-5-(4-{[ethyl-(2-hydroxy-ethyl)-amino]-methyl}-phenyl)-1H-[1,2,3]triazole-4-carboxylic acid ethylamide; 1-(2,4-dihydroxy-5-isopropyl-phenyl)-5-{4-[2-(2-hydroxy-ethyl)-piperidin-1-ylmethyl]-phenyl}-1H-[1,2,3]triazole-4-carboxylic acid ethylamide; 1-(2,4-dihydroxy-5-isopropyl-phenyl)-5-(4-piperidin-1-ylmethyl-phenyl)-1H-[1,2,3]triazole-4-carboxylic acid ethylamide; 5-(4-diethylaminomethyl-phenyl)-1-(2,4-dihydroxy-5-isopropyl-phenyl)-1H-[1,2,3]triazole-4-carboxylic acid ethylamide; 1-(2,4-dihydroxy-5-isopropyl-phenyl)-5-[4-(4-methyl-piperazin-1-ylmethyl)-phenyl]-1H-[1,2,3]triazole-4-carboxylic acid ethylamide; 1-(2,4-dihydroxy-5-isopropyl-phenyl)-5-(4-piperazin-1-ylmethyl-phenyl)-1H-[1,2,3]triazole-4-carboxylic acid ethylamide; 1-(2,4-dihydroxy-5-isopropyl-phenyl)-5-[4-(4-dimethylamino-piperidin-1-ylmethyl)-phenyl]-1H-[1,2,3]triazole-4-carboxylic acid ethylamide; 1-(2,4-dihydroxy-5-isopropyl-phenyl)-5-{4-[(2-morpholin-4-yl-ethylamino)-methyl]-phenyl}-1H-[1,2,3]triazole-4-carboxylic acid ethylamide; 5-{4-[(cyclohexylmethyl-amino)-methyl]-phenyl}-1-(2,4-dihydroxy-5-isopropyl-phenyl)-1H-[1,2,3]triazole-4-carboxylic acid ethylamide; 5-(4-cyclohexylaminomethyl-phenyl)-1-(2,4-dihydroxy-5-isopropyl-phenyl)-1H-[1,2,3]triazole-4-carboxylic acid ethylamide; 5-{4-[(2-diethylamino-ethylamino)-methyl]-phenyl}-1-(2,4-dihydroxy-5-isopropyl-phenyl)-1H-[1,2,3]triazole-4-carboxylic acid ethylamide; 5-{4-[(3-thethylamino-propylamino)-methyl]-phenyl}-1-(2,4-dihydroxy-5-isopropyl-phenyl)-1H-[1,2,3]triazole-4-carboxylic acid ethylamide; 1-(2,4-dihydroxy-5-isopropyl-phenyl)-5-{4-[(1-methyl-piperidin-4-ylamino)-methyl]-phenyl}-1H-[1,2,3]triazole-4-carboxylic acid ethylamide; 1-(2,4-dihydroxy-5-isopropyl-phenyl)-5-[4-((S)-3-dimethylamino-pyrrolidin-1-ylmethyl)-phenyl]-1H-[1,2,3]triazole-4-carboxylic acid ethylamide; 1-(2,4-dihydroxy-5-isopropyl-phenyl)-5-(4-pyrrolidin-1-ylmethyl-phenyl)-1H-[1,2,3]triazole-4-carboxylic acid ethylamide; 1-(2,4-dihydroxy-5-isopropyl-phenyl)-5-(4-imidazol-1-ylmethyl-phenyl)-1H-[1,2,3]triazole-4-carboxylic acid ethylamide; 4-isopropyl-6-[5-(4-morpholin-4-yl-phenylamino)-[1,2,3]triazol-1-yl]-benzene-1,3-diol; 4-isopropyl-6-[5-(4-morpholin-4-yl-benzylamino)-[1,2,3]triazol-1-yl]-benzene-1,3-diol; 1-(2,4-dihydroxy-5-isopropyl-phenyl)-5-(4-morpholin-4-yl-phenylamino)-1H-[1,2,3]triazole-4-carboxylic acid ethylamide; 1-(2,4-dihydroxy-5-isopropyl-phenyl)-5-(4-morpholin-4-yl-benzylamino)-1H-[1,2,3]triazole-4-carboxylic acid ethylamide; 1-(2,4-dihydroxy-5-isopropyl-phenyl)-5-(4-morpholin-4-ylmethyl-phenyl)-1H-[1,2,3]triazole-4-carboxylic acid hexylamide; 1-(2,4-dihydroxy-5-isopropyl-phenyl)-5-(4-morpholin-4-ylmethyl-phenyl)-1H-[1,2,3]triazole-4-carboxylic acid cyclopentylamide; 1-(2,4-dihydroxy-5-isopropyl-phenyl)-5-(4-morpholin-4-ylmethyl-phenyl)-1H-[1,2,3]triazole-4-carboxylic acid cyclohexylamide; [1-(2,4-dihydroxy-5-isopropyl-phenyl)-5-(4-morpholin-4-ylmethyl-phenyl)-1H-[1,2,3]triazol-4-yl]-morpholin-4-yl-methanone; (S)-2-{[1-(2,4-dihydroxy-5-isopropyl-phenyl)-5-(4-morpholin-4-ylmethyl-phenyl)-1H-[1,2,3]triazole-4-carbonyl]-amino}-3-methyl-butyric acid; 4-isopropyl-6-[5-(4-pyrrolidin-1-ylmethyl-phenyl)-[1,2,3]triazol-1-yl]-benzene-1,3-diol; 4-isopropyl-6-[5-(4-isoxazolidin-2-ylmethyl-phenyl)-[1,2,3]triazol-1-yl]-benzene-1,3-diol; 1-(2,4-dihydroxy-5-isopropyl-phenyl)-5-(4-isoxazolidin-2-ylmethyl-phenyl)-1H-[1,2,3]triazole-4-carboxylic acid ethylamide; 1-(2,4-dihydroxy-5-isopropyl-phenyl)-5-[4-(4-phenyl-piperazin-1-ylmethyl)-phenyl]-1H-[1,2,3]triazole-4-carboxylic acid ethylamide; 4-[5-(4-{[ethyl-(2-hydroxy-ethyl)-amino]-methyl}-phenyl)-[1,2,3]triazol-1-yl]-6-isopropyl-benzene-1,3-diol; 4-(5-{4-[2-(2-Hydroxy-ethyl)-piperidin-1-ylmethyl]-phenyl}-[1,2,3]triazol-1-yl)-6-isopropyl-benzene-1,3-diol; 4-isopropyl-6-[5-(4-piperidin-1-ylmethyl-phenyl)-[1,2,3]triazol-1-yl]-benzene-1,3-diol; 4-[5-(4-diethylaminomethyl-phenyl)-[1,2,3]triazol-1-yl]-6-isopropyl-benzene-1,3-diol; N-[3-(2,4-dihydroxy-5-isopropyl-phenyl)-3H-[1,2,3]triazol-4-yl]-4-morpholin-4-yl-benzamide; 1-(2,4-dihydroxy-5-isopropyl-phenyl)-5-(4-morpholin-4-yl-benzoylamino)-1H-[1,2,3]triazole-4-carboxylic acid ethylamide; N-[3-(2,4-dihydroxy-5-isopropyl-phenyl)-3H-[1,2,3]triazol-4-yl]-4-piperidin-1-yl-benzamide; 1-(2,4-dihydroxy-5-isopropyl-phenyl)-5-(4-piperidin-1-yl-benzoylamino)-1H-[1,2,3]triazole-4-carboxylic acid ethylamide; N-[3-(2,4-dihydroxy-5-isopropyl-phenyl)-3H-[1,2,3]triazol-4-yl]-4-(3-hydroxy-piperidin-1-yl)-benzamide; 1-(2,4-dihydroxy-5-isopropyl-phenyl)-5-[4-(3-hydroxy-piperidin-1-yl)-benzoylamino]-1H-[1,2,3]triazole-4-carboxylic acid ethylamide; N-[3-(2,4-dihydroxy-5-isopropyl-phenyl)-3H-[1,2,3]triazol-4-yl]-4-morpholin-4-ylmethyl-benzamide; 1-(2,4-dihydroxy-5-isopropyl-phenyl)-5-(4-morpholin-4-ylmethyl-benzoylamino)-1H-[1,2,3]triazole-4-carboxylic acid ethylamide; 4-morpholin-4-ylmethyl-cyclohexanecarboxylic acid [3-(2,4-dihydroxy-5-isopropyl-phenyl)-3H-[1,2,3]triazol-4-yl]-amide; 1-(2,4-dihydroxy-5-isopropyl-phenyl)-5-[(4-morpholin-4-ylmethyl-cyclohexanecarbonyl)-amino]-1H-[1,2,3]triazole-4-carboxylic acid ethylamide; 4-isopropyl-6-[5-[4-(4-methyl-piperazin-1-ylmethyl)-phenyl]-[1,2,3]triazol-1-yl]-benzene-1,3-diol; 4-isopropyl-6-[5-(4-morpholin-4-ylmethyl-phenyl)-[1,2,3]triazol-1-yl]-benzene-1,3-diol; 1-(2,4-dihydroxy-5-isopropyl-phenyl)-5-(4-morpholin-4-ylmethyl-phenyl)-1H-[1,2,3]triazole-4-carboxylic acid ethylamide; 5-[4-(4-benzyl-piperazin-1-ylmethyl)-phenyl]-1-(2,4-dihydroxy-5-isopropyl-phenyl)-1H-[1,2,3]triazole-4-carboxylic acid ethylamide; N-[3-(2,4-dihydroxy-5-isopropyl-phenyl)-3H-[1,2,3]triazol-4-yl]-4- pyrrolidin-1-yl-benzamide; 1-(2,4-dihydroxy-5-isopropyl-phenyl)-5-(4-pyrrolidin-1-yl-benzoylamino)-1H-[1,2,3]triazole-4-carboxylic acid ethylamide and 1-(2,4-dihydroxy-5-isopropyl-phenyl)-5-(4-morpholin-4-ylmethyl-phenyl)-1H-[1,2,3]triazole-4-carboxylic acid (2-chloro-ethyl)-amide.

Even more preferred compounds are the ones selected from the group consisting of 4-isopropyl-6-[5-(4-(morpholin-4-ylmethyl-phenyl)-[1,2,3]-triazol-1-yl)benzene-1,3-diol; 4-{5-[4-(3-hydroxy-piperidin-1-ylmethyl)-phenyl]-[1,2,3]triazol-1-yl}-6-isopropyl-benzene-1,3-diol; 4-{5-[4-(4-benzyl-piperazin-1-ylmethyl)-phenyl]-[1,2,3]triazol-1-yl}-6-isopropyl-benzene-1,3-diol; 4-isopropyl-6-{5-[4-(4-phenyl-piperazin-1-ylmethyl)-phenyl]-[1,2,3]triazol-1-yl}-benzene-1,3-diol; 1-(2,4-dihydroxy-5-isopropyl-phenyl)-5-(4-morpholin-4-ylmethyl-phenyl)-1H-[1,2,3]triazole-4-carboxylic ethyl amide; (R,S)-1-(2,4-dihydroxy-5-isopropyl-phenyl)-5-[4-(3-hydroxy-piperidin-1-ylmethyl)-phenyl]-1H-[1,2,3]triazole-4-carboxylic acid ethylamide; 1-(2,4-dihydroxy-5-isopropyl-phenyl)-5-(4-{[ethyl-(2-hydroxy-ethyl)-amino]-methyl}-phenyl)-1H-[1,2,3]triazole-4-carboxylic acid ethylamide; 1-(2,4-dihydroxy-5-isopropyl-phenyl)-5-{4-[2-(2-hydroxy-ethyl)-piperidin-1-ylmethyl]-phenyl}-1H-[1,2,3]triazole-4-carboxylic acid ethylamide; 1-(2,4-dihydroxy-5-isopropyl-phenyl)-5-(4-piperidin-1-yl-methyl-phenyl)-1H-[1,2,3]triazole-4-carboxylic acid ethylamide; 5-(4-diethylaminomethyl-phenyl)-1-(2,4-dihydroxy-5-isopropyl-phenyl)-1H-[1,2,3]triazole-4-carboxylic acid ethylamide; 1-(2,4-dihydroxy-5-isopropyl-phenyl)-5-[4-(4-methyl-piperazin-1-ylmethyl)-phenyl]-1H-[1,2,3]triazole-4-carboxylic acid ethylamide; 1-(2,4-dihydroxy-5-isopropyl-phenyl)-5-(4-piperazin-1-ylmethyl-phenyl)-1H-[1,2,3]triazole-4-carboxylic acid ethylamide; 1-(2,4-dihydroxy-5-isopropyl-phenyl)-5-[4-(4-dimethylamino-piperidin-1-ylmethyl)-phenyl]-1H-[1,2,3]triazole-4-carboxylic acid ethylamide; 1-(2,4-dihydroxy-5-isopropyl-phenyl)-5-{4-[(2-morpholin-4-yl-ethylamino)-methyl]-phenyl}-1H-[1,2,3]triazole-4-carboxylic acid ethylamide; 5-{4-[(cyclohexylmethyl-amino)-methyl]-phenyl}-1-(2,4-dihydroxy-5-isopropyl-phenyl)-1H-[1,2,3]triazole-4-carboxylic acid ethylamide; 5-(4-cyclohexylaminomethyl-phenyl)-1-(2,4-dihydroxy-5-isopropyl-phenyl)-1H-[1,2,3]triazole-4-carboxylic acid ethylamide; 5-{4-[(2-Diethylamino-ethylamino)-methyl]-phenyl}-1-(2,4-dihydroxy-5-isopropyl-phenyl)-1H-[1,2,3]triazole-4-carboxylic acid ethylamide; 5-{4-[(3-diethylamino-propylamino)-methyl]-phenyl}-1-(2,4-dihydroxy-5-isopropyl-phenyl)-1H-[1,2,3]triazole-4-carboxylic acid ethylamide; 1-(2,4-dihydroxy-5-isopropyl-phenyl)-5-{4-[(1-methyl-piperidin-4-ylamino)-methyl]-phenyl}-1H-[1,2,3]triazole-4-carboxylic acid ethylamide; 1-(2,4-dihydroxy-5-isopropyl-phenyl)-5-[4-((S)-3-dim ethyl amino-pyrrolidin-1-ylmethyl)-phenyl]-1H-[1,2,3]triazole-4-carboxylic acid ethylamide; 1-(2,4-dihydroxy-5-isopropyl-phenyl)-5-(4-pyrrolidin-1-ylmethyl-phenyl)-1H-[1,2,3]triazole-4-carboxylic acid ethylamide; 1-(2,4-dihydroxy-5-isopropyl-phenyl)-5-(4-imidazol-1-ylmethyl-phenyl)-1H-[1,2,3]triazole-4-carboxylic acid ethylamide; 4-isopropyl-6-[5-(4-morpholin-4-yl-phenylamino)-[1,2,3]triazol-1-yl]-benzene-1,3-diol; 4-isopropyl-6-[5-(4-morpholin-4-yl-benzylamino)-[1,2,3]triazol-1-yl]-benzene-1,3-diol; 1-(2,4-dihydroxy-5-isopropyl-phenyl)-5-(4-morpholin-4-yl-phenylamino)-1H-[1,2,3]triazole-4-carboxylic acid ethylamide; 1-(2,4-dihydroxy-5-isopropyl-phenyl)-5-(4-morpholin-4-yl-benzylamino)-1H-[1,2,3]triazole-4-carboxylic acid ethylamide; 1-(2,4-dihydroxy-5-isopropyl-phenyl)-5-(4-morpholin-4-ylmethyl-phenyl)-1H-[1,2,3]triazole-4-carboxylic acid hexylamide; 1-(2,4-dihydroxy-5-isopropyl-phenyl)-5-(4-morpholin-4-ylmethyl-phenyl)-1H-[1,2,3]triazole-4-carboxylic acid cyclopentylamide; 1-(2,4-dihydroxy-5-isopropyl-phenyl)-5-(4-morpholin-4-ylmethyl-phenyl)-1H-[1,2,3]triazole-4-carboxylic acid cyclohexylamide; [1-(2,4-dihydroxy-5-isopropyl-phenyl)-5-(4-morpholin-4-ylmethyl-phenyl)-1H-[1,2,3]triazol-4-yl]-morpholin-4-yl-methanone and (S)-2-{[1-(2,4-dihydroxy-5-isopropyl-phenyl)-5-(4-morpholin-4-ylmethyl-phenyl)-1H-[1,2,3]triazole-4-carbonyl]-amino}-3-methyl-butyric acid.

In a preferred embodiment, said medicament is used for treating cancer diseases where the cancer disease is a cancer of the breasts, pancreas, lung, pleura, colon, peritoneum, skin, face and neck, kidney, bladder, brain, prostate, cervix, ovaries, eyes or the cancer disease is a leukaemia or is a metastatic cancer.

In a further preferred embodiment, said medicament is used for treating metastatic cancer diseases.

In another preferred embodiment, said medicament is used for treating inflammatory diseases.

The following illustrated Examples are by no means an exhaustive list of what the present invention intends to protect.

EXAMPLES

Abbreviations:
AcOEt: ethyl acetate
AcOH: acetic acid
$BCl_3$: boron trichloride
Boc: t-butoxycarbonyl
bs: broad singlet
$ClCO_2Me$: methylchloroformiate
Cp*: pentamethylcyclopentadienyl
DCM: dichloromethane
DMF: dimethylformamide
DMSO: dimethylsulfoxide
EtOH: ethanol
$Et_2O$: diethyl ether
hept: heptuplet
KHDMS: potassium hexamethyldisilazane
LiHDMS: Lithium hexamethyldisilazane
MeOH: methanol
MsCl: methanesulfonyl chloride
$NH_4Cl$: ammonium chloride
PE: petroleum ether
quint: quintet
RT: room temperature
TBDMS: t-butyldimethylsilyl
TEA: triethylamine
TFA: trifluoroacetic acid
THF: tetrahydrofuran
TLC: thin layer chromatography
$TMSN_3$: trimethylsilyl azide General Remarks:

Reactions and product mixtures were routinely monitored by thin-layer chromatography (TLC) on silica gel $F_{254}$ Merck plates. Flash column chromatography was carried out using silica gel (Merck 230-400 mesh). Nuclear magnetic resonance ($^1H$ and $^{13}C$ NMR) spectra were gathered, with a Bruker AC-200 spectrometer or with a Varian Mercury Plus 300 or 400, and chemical shifts are given in part per million (ppm) downfield from tetramethylsilane as internal standard. The coupling constants are given in Hz.

All drying operations were performed over anhydrous sodium sulphate. Flash column chromatographies (medium pressure) were carried out using silica gel (Merck 230-400 mesh).

Example 1

4-isopropyl-6-[5-(4-(morpholin-4-ylmethyl-phenyl)- [1,2,3]-triazol-1-yl)benzene-1,3-diol STEP A: 1,5-bis-benzyloxy-2-isopropyl-4-nitro-benzene $HNO_3$ (1.11 ml, 13.7 mmol) was added to a suspension of 2,4-bis-benzyloxy-1-isopropyl-benzene (3.8 g, 11.44 mmol) in AcOH (46 ml) and the reaction was heated to 70-80° C. for 40 minutes. The solution was cooled down to 0° C. and neutralized with aq. $NaHCO_3$. The organic phase was extracted with AcOEt and the solvent was removed under reduced pressure. The crude reaction mixture was purified by flash chromatography (PE/AcOEt:95/5 to 90/10) and the title compound was obtained as a yellow solid.

Yield: 35% (1.51 g).

$^1$H NMR (400 MHz, $CDCl_3$) δ: 7.87 (s, 1H), 7.43-7.31 (m, 10H), 6.52 (s, 1H), 5.14 (s, 2H), 5.05 (s, 2H), 3.30-3.23 (m, 1H), 1.20 (d, J=7.2 Hz, 6H).

STEP B: 1,5-bis-benzyloxy-2-isopropyl-4-amino-benzene $SnCl_2.2 H_2O$ (5.38 g, 23.8 mmol) and HCl (4.7 ml, 56.8 mmol) were added to a suspension of 1,5-bis-benzyloxy-2-isopropyl-4-nitro-benzene (1.5 g, 3.98 mmol) in EtOH (38 ml). The reaction was heated to 80° C. for 4 hours before being cooled down to 0° C. A solution of NaOH (28 ml of a 20% water solution) was added. The salts precipitated were filtered off through a pad of Celite® and washed with AcOEt. The organic phase was extracted three times with AcOEt and the solvent was evaporated under reduced pressure to afford the desire adduct which was used in the next step without any further purification.

Yield: 80% (1.10 g)

STEP C: 1,5-bis-benzyloxy-2-isopropyl-4-azido-benzene tBuONO (2.25 ml, 19 mmol) and $TMSN_3$ (2 ml, 15.2 mmol) were added to a solution of 1,5-bis-benzyloxy-2-isopropyl-4-amino-benzene (1.10 g, 3.18 mmol) in $CH_3CN$ (40 ml). The reaction mixture was stirred for 1 hour at 0° C. and for 12 hours at RT. The solvent was evaporated under reduced pressure and the crude reaction mixture was purified by flash chromatography (PE/AcOEt:95/5 to 90/10). The title compound was obtained as a brown solid (890 mg, 75%).

Yield: 75% (0.89 g).

$^1$H NMR (400 MHz, $CDCl_3$) δ: 7.40-7.31 (m, 10H), 6.82 (s, 1H), 6.52 (s, 1H), 5.04 (s, 2H), 4.96 (s, 2H), 3.31-3.24 (m, 1H), 1.16 (d, J=6.8 Hz, 6H).

STEP D: {4-[3-(2,4-bis-benzyloxy-5-isopropyl-phenyl)-3H-[1,2,3]triazol-4-yl]-phenyl}-methanol 1,5-bis-benzyloxy-2-isopropyl-4-azido-benzene (890 mg, 2.38 mmol) was dissolved in DMF (5 ml) and (4-ethynylphenyl)-methanol (286 mg, 2.16 mmol) was added at RT. The flask was subjected to three vacuum-nitrogen cycles. [Cp*RuCl]4 was then added (116 mg, 0.11 mmol) and three further cycles were done. The reaction was left to RT until completion (monitored by TLC). AcOEt and water were then added. The organic phase was extracted four times with AcOEt, washed with water (three times) and brine (one time) and dried over $Na_2SO_4$; the solvent was removed under reduced pressure and the mixture was purified by column chromatography (PE/AcOEt: 60:40). The title compound was obtained as an oil.

Yield: 72% (866 mg).

$^1$H NMR (400 MHz, $CDCl_3$) δ: 7.85 (s, 1H), 7.36-7.14 (m, 13H), 6.87-6.83 (m, 2H), 6.45 (s, 1H), 4.97 (s, 2H), 4.71 (s, 2H), 4.69 (s, 2H), 3.32 (quint, J=6.8 Hz, 1H), 1.21 (s, 3H), 1.17 (s, 3H).

$^{13}$C NMR (100 MHz, $CDCl_3$) δ: 157.65, 151.46, 141.66, 139.27, 136.42, 136.09, 131.75, 130.62, 128.61, 128.37, 128.04, 127.83, 127.62, 127.11, 126.95, 126.69, 126.48, 125.84, 118.56, 99.08, 70.71, 70.31, 64.60, 26.44, 22.57.

STEP E: 4-{4-[3-(2,4-bis-benzyloxy-5-isopropyl-phenyl)-3H-[1,2,3]triazol-4-yl]-benzyl}-morpholine TEA (160 μl, 1.17 mmol) and MsCl (90 μl, 1.17 mmol) were added to a solution of {4-[3-(2,4-bis-benzyloxy-5-isopropyl-phenyl)-3H-[1,2,3]triazol-4-yl]-phenyl}-methanol (200 mg, 0.39 mmol) in DCM (5 ml) at 0° C. The solution was stirred for 30 minutes at 0° C. and for 12 hours at RT. The solvent was removed under reduced pressure and the reaction crude was dissolved in DMF (3 ml). Morpholine (1.17 mmol) and TEA (160 μl, 1.17 mmol) were added and the reaction mixture was stirred for 12 hours at RT. After standard work-up with AcOEt (4×30 ml) and washing with $H_2O$ (2×30 mL) and brine (2×30 ml), the solvent was evaporated under reduced pressure and the crude reaction mixture was purified by column chromatography (PE/AcOEt:20/80) to obtain the desired adduct as an oil.

Yield: 80% (179 mg).

$^1$H NMR (400 MHz, $CDCl_3$) δ: 7.85 (s, 1H), 7.38-7.15 (m, 13H), 6.90-6.88 (m, 2H), 6.47 (s, 1H), 4.99 (s, 2H), 4.72 (s, 2H), 3.73-3.63 (m, 4H), 3.52-3.40 (m, 2H), 3.35-3.27 (m, 1H), 2.43-2.33 (m, 4H), 1.16 (d, J=7.2 Hz, 6H).

STEP F: 4-isopropyl-6-[5-(4-(morpholin-4-ylmethyl-phenyl)-[1,2,3]triazol-1-yl]-benzene-1,3-diol 680 μl of $BCl_3$ (1 M solution in DCM) was added to a solution of 4-{4-[3-(2,4-bis-benzyloxy-5-isopropyl-phenyl)-3H-[1,2,3]triazol-4-yl]-benzyl}-morpholine (100 mg, 0.17 mmol) in dry DCM (3 ml) at 0° C. The mixture was stirred for 2 hours at RT. A saturated aqueous solution of $NaHCO_3$ was added (until the pH became slightly basic) and the organic phase was extracted with DCM (3×10 ml), washed with $H_2O$ and dried over $Na_2SO_4$. The solvent was removed under reduced pressure. The crude reaction mixture was purified by column chromatography (DCM/MeOH:95/5).

Yield: 68% (46 mg).

$^1$H NMR (400 MHz, MeOD) δ: 8.92 (s, 1H), 7.47 (s, 4H), 7.20 (s, 1H), 6.38 (s, 1H), 4.90 (bs, 2H), 3.82 (s, 2H), 3.75-3.68 (m, 4H), 3.25-3.12 (m, 1H), 2.78-2.70 (m, 4H), 1.15 (d, J=6.8 Hz, 6H).

Examples 2-4 have been synthesized following the procedure as described in example 1 and using the adequate amine in Step E instead of morpholine.

Example 2

4-{5-[4-(3-hydroxy-piperidin-1-ylmethyl)-phenyl]-[1,2,3]triazol-1-yl}-6-isopropyl-benzene-1,3-diol STEP E: 1-{4-[3-(2,4-bis-benzyloxy-5-isopropyl-phenyl)-3H-[1,2,3]triazol-4-yl]-benzyl}-piperidin-3-ol The title compound was obtained as an oil after purification by column chromatography (DCM/MeOH:95/5).

Yield: 85%.

$^1$H NMR (400 MHz, $CDCl_3$) δ: 7.84 (s, 1H), 7.37-7.18 (m, 11H), 7.12 (d, J=8.0 Hz, 2H), 6.90-6.88 (m, 2H), 6.47 (s, 1H), 4.98 (s, 2H), 4.71 (s, 2H), 3.81-3.75 (m, 1H), 3.47 (s, 2H), 3.35-3.27 (m, 1H), 2.50-2.20 (m, 4H), 1.80-1.47 (m, 4H), 1.17 (d, J=6.8 Hz, 6H).

STEP F: 4-{5-[4-(3-hydroxy-piperidin-1-ylmethyl)-phenyl]-[1,2,3]triazol-1-yl}-6-isopropyl-benzene-1,3-diol The title compound was obtained as an oil after purification by column chromatography (DCM/MeOH:90/10).

Yield: 66%.

$^1$H NMR (400 MHz, MeOD) δ: 8.93 (s, 1H), 7.49 (s, 4H), 7.21 (s, 1H), 6.40 (s, 1H), 4.88 (bs, 3H), 3.90 (s, 2H), 3.92-3.77 (m, 1H), 3.24-3.12 (m, 1H), 2.95-2.50 (m, 4H), 1.90-1.40 (m, 4H), 1.16 (d, J=6.8 Hz, 6H).

Example 3

4-{5-[4-(4-benzyl-piperazin-1-ylmethyl)-phenyl]-[1,2,3]triazol-1-yl}-6-isopropyl-benzene-1,3-diol STEP E: 1-benzyl-4-{4-[3-(2,4-bis-benzyloxy-5-isopropyl-phenyl)-3H-[1,2,3]triazol-4-yl]-benzyl}-piperazine The title compound was obtained as an oil after purification by column chromatography (PE/AcOEt:20/80).

Yield: 87%.

$^1$H NMR (400 MHz, CDCl$_3$) δ: 7.85 (s, 1H), 7.38-7.14 (m, 18H), 6.88-6.86 (m, 2H), 6.47 (s, 1H), 4.99 (s, 2H), 4.71 (s, 2H), 3.65-3.49 (m, 4H), 3.34-3.28 (m, 1H), 3.23-3.21 (m, 2H), 2.68-2.40 (m, 6H), 1.16 (d, J=7.2 Hz, 6H).

STEP F: 4-{5-[4-(4-benzyl-piperazin-1-ylmethyl)-phenyl]-[1,2,3]triazol-1-yl}-6-isopropyl-benzene-1,3-diol The title compound was obtained as an oil after purification by column chromatography (DCM/MeOH:90/10).

Yield: 85%.

$^1$H NMR (400 MHz, MeOD) δ: 10.26 (bs, 1H), 10.11 (bs, 1H), 9.24 (s, 1H), 7.43-7.29 (m, 10H), 6.54 (s, 1H), 3.48-3.31 (m, 6H), 3.13-3.06 (m, 1H), 2.42-2.32 (m, 6H), 1.08 (d, J=6.8 Hz, 6H).

Example 4

4-isopropyl-6-{5-[4-(4-phenyl-piperazin-1-ylmethyl)-phenyl]-[1,2,3]triazol-1-yl}-benzene-1,3-diol STEP E: 1-{4-[3-(2,4-bis-benzyloxy-5-isopropyl-phenyl)-3H-[1,2,3]triazol-4-yl]-benzyl}-4-phenyl-piperazine The title compound was obtained as an oil after purification by column chromatography (PE/AcOEt:20/80).

Yield: 89%.

$^1$H NMR (400 MHz, CDCl$_3$) δ: 7.85 (s, 1H), 7.40-7.14 (m, 15H), 6.93-6.82 (m, 5H), 6.47 (s, 1H), 4.98 (s, 2H), 4.72 (s, 2H), 3.60-3.50 (m, 2H), 3.37-3.15 (m, 5H), 2.62-2.52 (m, 4 ET), 1.16 (d, J=6.8 Hz, 6H).

STEP F: 4-isopropyl-6-{5-[4-(4-phenyl-piperazin-1-ylmethyl)-phenyl]-[1,2,3]triazol-1-yl}-benzene-1,3-diol The title compound was obtained as an oil after purification by column chromatography (DCM/MeOH:90/10).

Yield: 86%.

$^1$H NMR (400 MHz, DMSO) δ: 10.25 (bs, 1H), 10.09 (bs, 1H), 9.25 (s, 1H), 7.44-7.35 (m, 5H), 7.20-7.16 (m, 2H), 6.90-6.88 (m, 2H), 6.77-6.73 (m, 1H), 6.51 (s, 1H), 3.52 (s, 2H), 3.15-3.07 (m, 5H), 2.49-2.47 (m, 4H), 1.09 (d, J=6.8 Hz, 6H).

Example 5

1-(2,4-dihydroxy-5-isopropyl-phenyl)-5-(4-morpholin-4-ylmethyl-phenyl)-1H-[1,2,3]triazole-4-carboxylic ethyl amide STEP A: [4-(t-butyl-dimethyl-silanyloxymethyl)-phenyl]-propynoic acid methyl ester LiHMDS (5.8 ml, 1M in toluene) was added to a solution of t-butyl(4-ethynylbenzyloxy)dimethylsilane (820 mg, 3.33 mmol) in THF (28 ml) at −78° C. The reaction mixture was slowly warmed up to −40° C. and left for 1 hour at this temperature. A cooled solution (i.e., −40° C.) of ClCO$_2$Me (5.41 mmol in 9.6 ml THF) was added into the former solution and the reaction was warmed up to RT. A saturated solution of NH$_4$Cl was added to the reaction mixture. After standard work-up, the reaction mixture was purified by column chromatography (PE/AcOEt: 95/5) to give the title compound as yellow solid.

Yield: 76% (770 mg).

$^1$H NMR (400 MHz, CDCl$_3$) δ: 7.51 (d, J=8.0 Hz, 2H), 7.30 (d, J=8.0 Hz, 2H), 4.72 (s, 2H), 3.79 (s, 3H), 0.91 (s, 9H), 0.07 (s, 6H).

$^{13}$C NMR (100 MHz, CDCl$_3$) δ: 154.06, 144.20, 132.53, 125.54, 117.41, 86.35, 79.69, 63.99, 52.24, 25.45, 17.92, 5.77.

STEP B: 1-(2,4-bis-benzyloxy-5-isopropyl-phenyl)-5-[4-(t-butyl-dimethyl-silanyloxymethyl)-phenyl]-1H-[1,2,3]triazole-4-carboxylic acid methyl ester A DMF solution (2.5 ml) containing 1,5-bis-benzyloxy-2-isopropyl-4-azido-benzene (373 mg, 1 mmol) and [4-(tert-butyl-dimethyl-silanyloxymethyl)-phenyl]-propynoic acid methyl ester (277 mg, 0.91 mmol) was degassed at RT by means of three vacuum-nitrogen cycles. [Cp*RuCl]4 (49 mg, 0.045 mmol) was then added and other three cycles were done. The reaction was stirred at RT until completion (monitored by TLC). AcOEt and water were then added. After standard work-up, the crude reaction mixture was purified by column chromatography (PE/AcOEt:60/40) to get the desired adduct as an oil.

Yield: 68% (419 mg).

$^1$H NMR (400 MHz, CDCl$_3$) δ: 7.31-7.16 (m, 13H), 6.94 (d, J=7.2 Hz, 2H), 6.41 (s, 1H), 4.92 (s, 2H), 4.72 (s, 4H), 3.82 (s, 3H), 3.30-3.23 (m, 1H), 1.13 (d, J=6.8 Hz, 6H), 0.93 (s, 9H), 0.09 (s, 6H).

$^{13}$C NMR (100 MHz, CDCl$_3$) δ: 161.33, 157.47, 151.29, 142.60, 136.04, 135.67, 135.10, 129.84, 129.38, 128.18, 128.08, 127.59, 127.50, 126.69, 126.41, 125.62, 124.94, 124.07, 117.17, 98.50, 70.26, 69.93, 64.12, 51.45, 25.97, 25.55, 22.14, 17.97, 5.66.

STEP C: 1-(2,4-bis-benzyloxy-5-isopropyl-phenyl)-5-(4-hydroxymethyl-phenyl)-1H-[1,2,3]triazole-4-carboxylic acid methyl ester TBAF (270 mg, 1.25 mmol) was added to a solution of 1-(2,4-bis-benzyloxy-5-isopropyl-phenyl)-5-[4-(tert-butyl-climethyl-silanyloxymethyl)-phenyl]-1H-[1,2,3]triazole-4-carboxylic acid methyl ester (460 mg, 0.68 mmol) in THF (4 ml) and the reaction was stirred for 2 hours at RT. AcOEt (20 ml) was added and the organic phase was washed with a saturated solution of NH$_4$Cl and with H$_2$O; it was dried over Na$_2$SO$_4$ and the solvent was removed under reduced pressure and the crude reaction mixture was purified by column chromatography (PE/AcOEt:40/60). The title compound was obtained as an oil.

Yield: 80% (310 mg).

$^1$H NMR (400 MHz, CDCl$_3$) δ: 7.29-7.15 (m, 13H), 6.93 (d, J=6.8 Hz, 2H), 6.37 (s, 1H), 4.89 (s, 2H), 4.70 (s, 2H), 4.62 (s, 2H), 3.79 (s, 3H), 3.31-3.18 (m, 1H), 1.12 (d, J=6.8 Hz, 6H).

$^{13}$C NMR (100 MHz, CDCl$_3$) δ: 161.35, 157.57, 151.25, 142.69, 142.59, 136.01, 135.64, 135.10, 129.92, 129.53, 128.27, 128.16, 127.70, 127.63, 126.78, 126.45, 125.74, 125.62, 124.30, 116.98, 98.40, 70.33, 69.91, 63.87, 51.66, 26.04, 22.20.

STEP D: 1-(2,4-bis-benzyloxy-5-isopropyl-phenyl)-5-(4-methanesulfonyloxy-methyl-phenyl)-1H-[1,2,3]triazole-4-carboxylic acid methyl ester TEA (230 μl, 1.65 mmol) and MsCl (130 μl, 1.65 mmol) were added to a solution of 1-(2,4-bis-benzyloxy-5-isopropyl-phenyl)-5-(4-hydroxymethyl-phenyl)-1H-[1,2,3]triazole-4-carboxylic acid methyl ester (310 mg, 0.55 mmol) in DCM (7 ml) at 0° C. The solution was stirred for 30 minutes at 0° C. and for 12 hours at RT. The solvent was removed under reduced pressure and the crude reaction mixture was dissolved in DMF (3-4 ml). The mesylate derivative thus obtained was used without any further purification in the next step.

STEP E: 1-(2,4-bis-benzyloxy-5-isopropyl-phenyl)-5-(4-morpholin-4-ylmethyl-phenyl)-1H-[1,2,3]triazole-4-carboxylic acid methyl ester Morpholine (1.65 mmol) and TEA (230 μl, 1.65 mmol) were added to the solution from Step D and the reaction mixture was stirred for 12 hours at RT. The reaction mixture was diluted with $H_2O$ and AcOEt. After standard work-up the reaction mixture was purified by column chromatography (DCM/MeOH:98/2) to get the desired adduct as an oil.

Yield: 60% (210 mg).

$^1$H NMR (400 MHz, CDCl$_3$) δ: 7.37-7.22 (m, 10H), 7.17 (d, J=8.4 Hz, 2H), 7.08 (s, 1H), 7.01-6.99 (m, 2H), 6.40 (s, 1H), 4.93 (s, 2H), 4.74 (s, 2H), 3.88 (s, 3H), 3.67 (t, J=4.4 Hz, 4H), 3.47 (s, 2H), 3.24 (quint, J=6.8 Hz, 1H), 2.42-2.38 (m, 4H), 1.10 (d, J=6.8 Hz, 6H).

STEP F: 1-(2,4-bis-benzyloxy-5-isopropyl-phenyl)-5-(4-morpholin-4-ylmethyl-phenyl)-1H-[1,2,3]triazole-4-carboxylic acid ethylamide EtNH$_2$ (1.5 ml of a solution 2 M in MeOH) was added to compound 1-(2,4-bis-benzyloxy-5-isopropyl-phenyl)-5-(4-morpholin-4-ylmethyl-phenyl)-1H-[1,2,3]triazole-4-carboxylic acid methyl ester (0.15 mmol) and the mixture was heated to 80° C. for 24 hours in a sealed tube. The solvent and the excess of amine were removed under reduced pressure and the residue thus obtained was used in the next step without any purification.

STEP G: 1-(2,4-dihydroxy-5-isopropyl-phenyl)-5-(4-morpholin-4-ylmethyl-phenyl)-1H-[1,2,3]triazole-4-carboxylic acid ethylamide Pd(OH)$_2$/C (0.01 mmol) was added to the intermediate obtained in Step F (0.1 mmol) dissolved in EtOH (5 ml) and the resulting mixture was subjected to hydrogenation under one atmosphere of hydrogen for 1 hour. The catalyst was filtered off through a Celite® pad and the ethanol was removed under reduced pressure. The reaction mixture was purified by column chromatography (DCM/MeOH:90/10) to obtain the title compound as an oil.

Yield: 68% (65 mg).

$^1$H NMR (400 MHz, MeOD) δ: 7.30-7.25 (m, 4H), 6.82 (s, 1H), 6.31 (s, 1H), 4.84 (bs, 3H), 3.63-3.61 (m, 4H), 3.46 (s, 2H), 3.37 (q, J=7.2 Hz, 2H), 3.10 (quint, J=6.8 Hz, 1H), 2.41-2.39 (m, 4H), 1.19 (t, J=7.2 Hz, 3H), 1.03 (d, J=6.8 Hz, 6H).

$^{13}$C NMR (100 MHz, MeOD) δ: 161.09, 156.58, 150.82, 140.08, 137.82, 137.43, 129.40, 128.18, 126.34, 125.10, 125.01, 114.40, 101.86, 65.82, 62.04, 52.74, 33.24, 25.52, 21.13, 13.20.

Examples 6-17 have been synthesized following the procedure as described in example 5 and using the adequate amine in Step E instead of morpholine.

Example 6

(R,S)-1-(2,4-dihydroxy-5-isopropyl-phenyl)-5-[4-(3-hydroxy-piperidin-1-ylmethyl)-phenyl]-1H-[1,2,3]triazole-4-carboxylic acid ethylamide STEP E: (R,S)-1-(2,4-bis-benzyloxy-5-isopropyl-phenyl)-5-[4-(3-hydroxy-piperidin-1-ylmethyl)-phenyl]-1H-[1,2,3]triazole-4-carboxylic acid methyl ester The title compound was obtained as an oil after purification by column chromatography (DCM/MeOH:96/4).

Yield: 74% (262 mg).

$^1$H NMR (400 MHz, CDCl$_3$) δ: 7.37-7.22 (m, 8H), 7.16 (AB system, 8.4 Hz, 4H), 7.09 (s, 1H), 7.00-6.98 (m, 2H), 6.40 (s, 1H), 4.92 (s, 2H), 4.72 (s, 2H), 3.85 (s, 3H), 3.78-3.74 (m, 1H), 3.45 (s, 2H), 3.24 (quint, J=6.8 Hz, 1H), 2.52-2.20 (m, 4H), 1.75-1.42 (m, 4H), 1.10 (d, J=6.8 Hz, 6H).

STEP G: (R,S)-1-(2,4-dihydroxy-5-isopropyl-phenyl)-5-[4-(3-hydroxy-piperidin-1-ylmethyl)-phenyl]-1H-[1,2,3]triazole-4-carboxylic acid ethylamide The title compound was obtained as an oil after purification by column chromatography (DCM/MeOH:90/10).

Yield: 63% (107 mg).

$^1$H NMR (400 MHz, MeOD) δ: 7.29 (AB system, J=8.0 Hz, 4H), 6.85 (s, 1H), 6.33 (s, 1H), 4.85 (bs, 3H), 3.66-3.61 (m, 1H), 3.51 (s, 2H), 3.39 (q, J=7.2 Hz, 2H), 3.11 (quint, J=6.8 Hz, 1H), 2.87-2.84 (m, 1H), 2.64-2.61 (m, 1H), 2.01-1.85 (m, 3H), 1.70-1.67 (m, 1H), 1.54-1.44 (m, 1H), 1.22 (t, J=7.2 Hz, 3H), 1.04 (d, J=6.8 Hz, 6H).

$^{13}$C NMR (100 MHz, MeOD) δ: 161.11, 156.59, 150.82, 140.08, 137.95, 137.47, 129.37, 128.23, 126.38, 125.03, 114.44, 101.96, 65.91, 61.79, 59.85, 52.30, 33.27, 31.96, 25.54, 22.01, 21.18, 13.21.

Example 7

1-(2,4-dihydroxy-5-isopropyl-phenyl)-5-(4-{[ethyl-(2-hydroxy-ethyl)-amino]-methyl}-phenyl)-1H-[1,2,3]triazole-4-carboxylic acid ethylamide STEP E: 1-(2,4-bis-benzyloxy-5-isopropyl-phenyl)-5-(4-{[ethyl-(2-hydroxy-ethyl)-amino]-methyl}-phenyl)-1H-[1,2,3]triazole-4-carboxylic acid methyl ester The title compound was obtained as an oil after purification by column chromatography (DCM/MeOH:98/2).

Yield: 53% (184 mg).

$^1$H NMR (400 MHz, CDCl$_3$) δ: 7.37-7.17 (m, 12H), 7.13 (s, 1H), 7.03-6.98 (m, 2H), 6.40 (s, 1H), 4.94 (s, 2H), 4.72 (s, 2H), 3.88 (s, 3H), 3.58 (s, 2H), 3.52 (t, J=5.2 Hz, 2H), 3.26 (quint, J=6.8 Hz, 1H), 2.64-2.32 (m, 4H), 1.12 (d, J=6.8 Hz, 6H), 1.01 (t, J=6.8 Hz, 3H).

STEP G: 1-(2,4-dihydroxy-5-isopropyl-phenyl)-5-(4-{[ethyl-(2-hydroxy-ethyl)-amino]-methyl}-phenyl)-1H-[1,2,3]triazole-4-carboxylic acid ethylamide The title compound was obtained as an oil after purification by column chromatography (DCM/MeOH:90/10).

Yield: 72% (132 mg).

$^1$H NMR (400 MHz, CDCl$_3$) δ: 7.30 (s, 5H), 6.85 (s, 1H), 6.33 (s, 1H), 4.88 (bs, 4H), 3.63 (s, 2H), 3.60 (t, J=6.2 Hz, 2H), 3.39 (q, J=7.2 Hz, 2H), 3.11 (quint, J=6.8 Hz, 1H), 2.61 (t, J=6.2 Hz, 2H), 2.54 (q, J=7.2 Hz, 2H), 1.21 (t, J=7.2 Hz, 3H), 1.07 (d, J=6.8 Hz, 6H), 1.02 (t, J=7.2 Hz, 3H).

$^{13}$C NMR (100 MHz, MeOD) δ: 161.14, 156.59, 150.87, 140.14, 139.64, 137.43, 129.34, 127.85, 126.35, 125.00, 124.74, 114.47, 101.98, 58.65, 57.29, 54.29, 47.00, 33.28, 25.55, 21.18, 13.21, 9.91.

Example 8

1-(2,4-dihydroxy-5-isopropyl-phenyl)-{4-[2-(2-hydroxy-ethyl)-piperidin-1-ylmethyl]-phenyl}-1H-[1,2,3]triazole-4-carboxylic acid ethylamide STEP E: 1-(2,4-bis-benzyloxy-5-isopropyl-phenyl)-{4-[2-(2-hydroxy-ethyl)-piperidin-1-ylmethyl]-phenyl}-1H-[1,2,3]triazole-4-carboxylic acid methyl ester The title compound was obtained as an oil after purification by column chromatography (DCM/MeOH:96/4).

Yield: 88% (325 mg).

$^1$H NMR (400 MHz, CDCl$_3$) δ: 7.39-7.22 (m, 8H), 7.19 (AB system, J=8.0 Hz, 4H), 7.10 (s, 1H), 7.04-7.02 (m, 2H), 6.42 (s, 1H), 4.96 (s, 2H), 4.75 (s, 2H), 4.16 (d, J=13.2 Hz, 1H), 3.92-3.90 (s, 3H and m, 1H), 3.73-3.68 (m, 1H), 3.40 (d, J=13.2 Hz, 1H), 3.25 (quint, J=6.8 Hz, 1H), 2.91-2.86 (m, 1H), 2.67-2.71 (m, 1H), 2.15-2.11 (m, 1H), 1.90-1.32 (m, 8H), 1.12 (d, J=6.8 Hz, 6H).

STEP G: 1-(2,4-dihydroxy-5-isopropyl-phenyl)-5-{4-[2-(2-hydroxy-ethyl)-piperidin-1-ylmethyl]-phenyl}-1H-[1,2,3]triazole-4-carboxylic acid ethylamide The title compound was obtained as an oil after purification by column chromatography (DCM/MeOH:88/12).

Yield: 58% (188 mg).

$^1$H NMR (400 MHz, CDCl$_3$) δ: 7.36 (s, 5H), 6.85 (s, 1H), 6.33 (s, 1H), 4.83 (bs, 4H), 4.17 (d, J=13.2 Hz, 1H), 3.72-3.59 (m, 2H), 3.56 (t, J=13.2 Hz, 1H), 3.39 (q, J=7.2 Hz, 2H), 3.10 (quint, J=6.8 Hz, 1H), 2.87-2.84 (m, 1H), 2.76-2.72 (m, 1H), 2.35-2.31 (m, 1H), 2.08-2.03 (m, 1H), 1.82-1.35 (m, 7H), 1.20 (t, J=7.2 Hz, 3H), 1.03 (d, J=6.8 Hz, 6H).

$^{13}$C NMR (100 MHz, MeOD) δ: 161.4, 150.2, 149.7, 144.0, 141.0, 131.8, 127.8, 127.41, 126., 122.4, 119.7, 105.7, 63.3, 61.7, 59.8, 36.9, 36.2, 31.8, 30.6, 22.76, 22.73, 14.71.

Example 9

1-(2,4-dihydroxy-5-isopropyl-phenyl)-5-(4-piperidin-1-ylmethyl-phenyl)-1H-[1,2,3]triazole-4-carboxylic acid ethylamide STEP E: 1-(2,4-bis-benzyloxy-5-isopropyl-phenyl)-5-(4-piperidin-1-ylmethyl-phenyl)-1H-[1,2,3]triazole-4-carboxylic acid methyl ester The title compound was obtained as an oil after purification by column chromatography (DCM/MeOH:98/2).

Yield: 84% (291 mg).

$^1$H NMR (400 MHz, CDCl$_3$) δ: 7.39-7.25 (m, 8H), 7.20 (AB system, J=8.4 Hz, 4H), 7.11 (s, 1H), 7.03-7.01 (m, 2H), 6.41 (s, 1H), 4.95 (s, 2H), 4.75 (s, 2H), 3.90 (s, 3H), 3.44 (s, 2H), 3.26 (quint, J=6.8 Hz, 1H), 2.37-2.33 (m, 4H), 1.55 (t, J=5.2 Hz, 4H), 1.45-1.41 (m, 2H), 1.12 (d, J=6.8 Hz, 6H).

STEP G: 1-(2,4-dihydroxy-5-isopropyl-phenyl)-5-(4-piperidin-1-ylmethyl-phenyl)-1H-[1,2,3]triazole-4-carboxylic acid ethylamide The title compound was obtained as an oil after purification by column chromatography (DCM/MeOH:90/10).

Yield: 65% (189 mg).

$^1$H NMR (400 MHz, CDCl$_3$) δ: 7.31 (AB system, J=8.6 Hz, 4H), 6.84 (s, 1H), 6.33 (s, 1H), 4.87 (bs, 3H), 3.59 (s, 2H), 3.39 (q, J=7.2 Hz, 2H), 3.10 (quint, J=6.8 Hz, 1H), 2.53-2.49 (m, 4H), 1.61-1.57 (m, 4H), 1.49-1.45 (m, 2H), 1.21 (t, J=7.2 Hz, 3H), 1.06 (d, J=6.8 Hz, 6H).

$^{13}$C NMR (100 MHz, MeOD) δ: 161.05, 156.63, 150.91, 139.96, 137.49, 136.33, 129.49, 128.76, 126.35, 125.61, 125.00, 114.39, 101.95, 61.92, 53.25, 33.27, 25.54, 24.16, 22.82, 21.16, 13.21.

Example 10

5-(4-diethylaminomethyl-phenyl)-1-(2,4-dihydroxy-5-isopropyl-phenyl)-1H-[1,2,3]triazole-4-carboxylic acid ethylamide STEP E: 1-(2,4-bis-benzyloxy-5-isopropyl-phenyl)-5-(4-diethylaminomethyl-phenyl)-1H-[1,2,3]triazole-4-carboxylic acid methyl ester The title compound was obtained as an oil after purification by column chromatography (DCM/MeOH:98/2).

Yield: 45% (153 mg).

$^1$H NMR (400 MHz, CDCl$_3$) δ: 7.37-7.26 (m, 8H), 7.20 (AB system, J=8.0 Hz, 4H), 7.11 (s, 1H), 7.04-7.02 (m, 2H), 6.40 (s, 1H), 4.95 (s, 2H), 3.90 (s, 3H), 3.54 (s, 2H), 3.26 (quint, J=6.8 Hz, 1H), 2.50 (q, J=7.2 Hz, 4H), 1.12 (d, J=6.8 Hz, 6H), 1.01 (t, J=7.2 Hz, 6H).

STEP G: 5-(4-diethylaminomethyl-phenyl)-1-(2,4-dihydroxy-5-isopropyl-phenyl)-1H-[1,2,3]triazole-4-carboxylic acid ethylamide The title compound was obtained as an oil after purification by column chromatography (DCM/MeOH:90/10).

Yield: 55% (84 mg).

$^1$H NMR (400 MHz, CDCl$_3$) δ: 7.33 (AB system, J=8.4 Hz, 4H), 6.84 (s, 1H), 6.32 (s, 1H), 4.83 (bs, 3H), 3.73 (s, 2H), 3.39 (q, J=7.2 Hz, 2H), 3.10 (quint, J=6.8 Hz, 1H), 2.65 (q, J=7.2 Hz, 4H), 1.21 (t, J=7.2 Hz, 3H), 1.11-1.06 (m, 12H).

$^{13}$C NMR (100 MHz, MeOD) δ: 161.4, 150.1, 149.2, 144.3, 143.8, 129.9, 128.1, 128.1, 127.3, 126.5, 122.0, 119.7, 105.6, 61.2, 46.7, 36.2, 25.2, 22.7, 14.7, 11.9.

Example 11

1-(2,4-dihydroxy-5-isopropyl-phenyl)-5-[4-(4-methyl-piperazin-1-ylmethyl)-phenyl]-1H-[1,2,3]triazole-4-carboxylic acid ethylamide STEP E: 1-(2,4-bis-benzyloxy-5-isopropyl-phenyl)-5-[4-(4-methyl-piperazin-1-ylmethyl)-phenyl]-1H-[1,2,3]triazole-4-carboxylic acid methyl ester The title compound was obtained as an oil after purification by column chromatography (DCM/MeOH:98/2).

Yield: 62% (162 mg).

$^1$H NMR (400 MHz, CDCl$_3$) δ: 7.28-7.15 (m, 12H), 7.09 (s, 1H), 7.01-7.00 (m, 2H), 6.40 (s, 1H), 4.94 (s, 2H), 4.74 (s, 2H), 3.88 (s, 3H), 3.46 (s, 2H), 3.28-3.21 (m, 1H), 2.50-2.35 (m, 8H), 2.26 (s, 6H), 1.10 (d, J=6.8 Hz, 6H).

$^{13}$C NMR (100 MHz, CDCl$_3$) δ: 161.35, 157.35, 151.38, 142.46, 139.51, 135.95, 135.64, 134.97, 130.00, 129.34, 128.20, 128.09, 128.01, 127.63, 127.57, 126.66, 126.40, 125.61, 124.15, 117.28, 98.55, 70.45, 69.91, 62.16, 54.63, 52.69, 51.55, 45.55, 25.88, 22.09.

STEP G: 1-(2,4-dihydroxy-5-isopropyl-phenyl)-5-[4-(4-methyl-piperazin-1-ylmethyl)-phenyl]-1H-[1,2,3]triazole-4-carboxylic acid ethylamide The title compound was obtained as a white solid after purification by column chromatography (DCM/MeOH:88/12).

Yield: 46% (73 mg).

$^1$H NMR (400 MHz, MeOD) δ: 7.29 (AB system, J=8.0 Hz, 4H), 6.84 (s, 1H), 6.33 (s, 1H); 3.50 (s, 2H), 3.39 (q, J=7.2 Hz, 2H), 3.14-3.07 (m, 1H), 2.60-2.40 (m, 8H), 2.32 (s, 3H), 1.21 (t, J=7.2 Hz, 3H), 1.06 (d, J=6.4 Hz, 6H).

$^{13}$C NMR (100 MHz, MeOD) δ: 161.07, 156.58, 150.82, 140.04, 138.01, 137.44, 129.42, 128.07, 126.33, 125.12, 124.99, 114.42, 101.91, 61.41, 53.67, 51.38, 43.83, 33.24, 25.53, 21.14, 13.20.

Example 12

1-(2,4-dihydroxy-5-isopropyl-phenyl)-5-(4-piperazin-1-ylmethyl-phenyl)-1H-[1,2,3]triazole-4-carboxylic acid ethylamide STEP E: 5-[4-(4-benzyl-piperazin-1-ylmethyl)-phenyl]-1-(2,4-bis-benzyloxy-5-isopropyl-phenyl)-1H-[1,2,3]triazole-4-carboxylic acid methyl ester The title compound was obtained as an oil after purification by column chromatography (DCM/MeOH:98/2).

Yield: 80% (317 mg).

$^1$H NMR (400 MHz, CDCl$_3$) δ: 7.27-7.16 (m, 17H), 7.11 (s, 1H), 7.02-7.00 (m, 2H), 6.43 (s, 1H); 4.94 (s, 2H), 4.74 (s, 2H), 3.87 (s, 3H), 3.51 (s, 2H), 3.49 (s, 2H), 3.30-3.25 (m, 1H), 3.20 (t, J=4.8 Hz, 4H), 2.51 (t, J=4.8 Hz, 4H), 1.12 (d, J=7.2 Hz, 6H).

$^{13}$C NMR (100 MHz, CDCl$_3$) δ: 161.35, 157.39, 151.39, 142.47, 139.58, 137.70, 136.01, 135.68, 134.98, 129.94, 129.35, 128.76, 128.65, 128.21, 128.10, 127.96, 127.78, 127.58, 126.92, 126.70, 126.44, 125.60, 124.13, 117.26, 99.55, 70.41, 69.91, 62.61, 62.16, 52.77, 51.81, 45.49, 25.92, 22.15.

STEP G: 1-(2,4-dihydroxy-5-isopropyl-phenyl)-5-(4-piperazin-1-ylmethyl-phenyl)-1H-[1,2,3]triazole-4-carboxylic acid ethylamide The title compound was obtained as a white solid after purification by column chromatography (DCM/MeOH:3/1).

Yield: 40% (71 mg).

$^1$H NMR (100 MHz, MeOD) δ: 7.30 (AB system, J=8.0 Hz, 4H), 6.84 (s, 1H), 6.35 (s, 1H), 3.53 (s, 2H), 3.39 (q, J=7.2 Hz, 2H), 3.17-3.07 (m, 1H), 3.04 (t, J=4.8 Hz, 4H), 2.55 (t, J=4.8 Hz, 4H), 1.21 (t, J=7.2 Hz, 3H), 1.06 (d, J=6.8 Hz, 6H).

$^{13}$C NMR (100 MHz, CDCl$_3$) δ: 161.08, 156.61, 150.91, 140.01, 137.96, 137.49, 129.46, 127.93, 126.29, 125.17, 124.98, 114.40, 101.96, 61.47, 50.30, 43.48, 33.24, 25.52, 21.14, 13.18.

Example 13

1-(2,4-dihydroxy-5-isopropyl-phenyl)-5-[4-(4-dimethylamino-piperidin-1-ylmethyl)-phenyl]-1H-[1,2,3]triazole-4-carboxylic acid ethylamide STEP E: 1-(2,4-bis-benzyloxy-5-isopropyl-phenyl)-5-[4-(4-dimethylamino-piperidin-1-ylmethyl)-phenyl]-1H-[1,2,3]triazole-4-carboxylic acid methyl ester The title compound was obtained as an oil after purification by column chromatography (DCM/MeOH:93/7).

Yield: 58% (214 mg).

$^1$H NMR (400 MHz, CDCl$_3$) δ: 7.37-7.15 (m, 12H), 7.09 (s, 1H), 7.02-7.00 (m, 2H), 6.41 (s, 1H), 4.94 (s, 2H), (4.75 (s, 2H), 3.89 (s, 3H), 3.45 (s, 2H), 3.28-3.21 (m, 1H), 2.88 (d, J=11.2 Hz, 2H), 2.29 (s, 6H), 2.22-2.16 (m, 1H), 1.95 (t, J=11.2 Hz, 2H), 1.78 (d, J=12.0 Hz, 2H), 1.57-1.48 (m, 2H), 1.11 (d, J=6.8 Hz, 6H).

$^{13}$C NMR (100 MHz, CDCl$_3$) δ: 161.38, 157.35, 151.38, 142.48, 139.83, 135.94, 135.64, 134.96, 130.03, 129.32, 128.20, 128.10, 127.91, 127.63, 127.57, 126.67, 126.40, 125.62, 124.06, 117.31, 98.56, 70.46, 69.93, 62.11, 61.93, 52.60, 51.56, 41.06, 27.68, 25.90, 22.10.

STEP G: 1-(2,4-dihydroxy-5-isopropyl-phenyl)-5-[4-(4-dimethylamino-piperidin-1-ylmethyl)-phenyl]-1H-[1,2,3]triazole-4-carboxylic acid ethylamide The title compound was obtained as a white solid after purification by column chromatography (gradient DCM/MeOH:2/6 to 100% MeOH).

Yield: 67% (107 mg).

$^1$H NMR (400 MHz, MeOD) δ: 7.29 (AB system, J=7.8 Hz, 4H), 6.76 (s, 1H), 6.20 (s, 1H), 3.46 (s, 2H), 3.39 (q, J=7.2 Hz, 2H), 3.12-3.05 (m, 1H), 2.89 (d, J=11.6 Hz, 2H), 2.25 (s, 6H), 2.19-2.13 (m, 1H), 1.97 (t, J=11.6 Hz, 2H), 1.80 (d, J=11.6 Hz, 2H), 1.52-1.44 (m, 2H), 1.21 (t, J=7.2 Hz, 3H), 1.04 (d, J=6.8 Hz, 6H).

$^{13}$C NMR (100 MHz, MeOD) δ: 161.18, 156.69, 152.27, 140.03, 138.11, 137.41, 129.40, 128.20, 125.53, 125.11, 124.79, 114.65, 102.75, 61.55, 51.91, 39.88, 33.24, 26.94, 25.45, 21.22, 13.18.

Example 14

1-(2,4-dihydroxy-5-isopropyl-phenyl)-5-{4-[(2-morpholin-4-yl-ethylamino)-methyl]-phenyl}-1H-[1,2,3]triazole-4-carboxylic acid ethylamide STEP E: 1-(2,4-bis-benzyloxy-5-isopropyl-phenyl)-5-{4-[(2-morpholin-4-yl-ethylamino)-methyl]-phenyl}-1H-[1,2,3]triazole-4-carboxylic acid methyl ester The title compound was obtained as an oil after purification by column chromatography (DCM/MeOH:95/5).

Yield: 33% (122 mg).

$^1$H NMR (400 MHz, CDCl$_3$) δ: 7.38-7.18 (m, 12H), 7.14 (s, 1H), 7.01-6.99 (m, 2H), 6.40 (s, 1H), 4.94 (s, 2H), 4.76 (s, 2H), 3.89 (s, 3H), 3.82 (s, 2H), 3.65 (t, J=4.4 Hz, 4H), 3.29-3.22 (m, 1H), 2.71 (t, J=5.8 Hz, 2H), 2.49 (t, J=5.8 Hz, 2H), 2.39 (t, J=4.4 Hz, 4H), 1.13 (d, J=6.8 Hz, 6H).

$^{13}$C NMR (100 MHz, CDCl$_3$) δ: 161.31, 157.44, 151.33, 142.47, 140.84, 135.93, 135.61, 135.07, 130.04, 129.56, 128.22, 128.11, 127.65, 127.59, 127.15, 126.70, 126.41, 125.65, 124.30, 117.22, 98.51, 70.47, 69.92, 66.51, 57.42, 53.22, 52.99, 51.57, 44.86, 25.94, 22.10.

STEP G: 1-(2,4-dihydroxy-5-isopropyl-phenyl)-5-{4-[(2-morpholin-4-yl-ethylamino)-methyl]-phenyl}-1H-[1,2,3]triazole-4-carboxylic acid ethylamide The title compound was obtained as a white solid after purification by column chromatography (DCM/MeOH:4/1).

Yield: 43% (40 mg).

$^1$H NMR (400 MHz, CDCl$_3$) δ: 7.33 (AB system, J=8.0 Hz, 4H), 6.89 (s, 1H), 6.31 (s, 1H), 3.84 (s, 2H), 3.65 (t, J=4.4 Hz, 4H), 3.39 (q, J=7.2 Hz, 2H), 3.14-3.07 (m, 1H), 2.72 (t, J=6.4 Hz, 2H), 2.48 (t, J=6.4 Hz, 2H), 2.38 (t, J=4.4 Hz, 4H), 1.21 (t, J=7.2 Hz, 3H), 1.08 (d, J=6.8 Hz, 6H).

$^{13}$C NMR (100 MHz, CDCl$_3$) δ: 161.08, 156.66, 150.87, 140.01, 138.41, 137.60, 129.71, 127.33, 126.31, 125.48, 125.09, 114.39, 101.87, 65.95, 55.99, 52.85, 51.56, 43.43, 33.23, 25.57, 21.14, 13.18.

Example 15

5-{4-[(cyclohexylmethyl-amino)-methyl]-phenyl}-1-(2,4-dihydroxy-5-isopropyl-phenyl)-1H-[1,2,3]triazole-4-carboxylic acid ethylamide STEP E: 1-(2,4-bis-benzyloxy-5-isopropyl-phenyl)-5-{4-[(cyclohexylmethyl-amino)-methyl]-phenyl}-1H-[1,2,3]triazole-4-carboxylic acid methyl ester The title compound was obtained as an oil after purification by column chromatography (DCM/MeOH:95/5).

Yield: 35% (126 mg).

$^1$H NMR (400 MHz, CDCl$_3$) δ: 7.38-7.17 (m, 12H), 7.14 (s, 1H), 7.00-6.98 (m, 2H), 6.39 (s, 1H), 4.94 (s, 2H), 4.75 (s, 2H), 3.89 (s, 3H), 3.76 (s, 2H), 3.28-3.25 (m, 1H), 2.45 (d, J=6.4 Hz, 2H), 1.75-1.64 (m, 5H), 1.50-1.43 (m, 2H), 1.25-1.18 (m, 2H), 1.14 (d, J=7.2 Hz, 6H), 0.94-0.85 (m, 2H).

$^{13}$C NMR (100 MHz, CDCl$_3$) δ: 161.36, 157.39, 151.31, 142.59, 141.90, 135.96, 135.65, 135.03, 130.00, 129.43, 128.21, 128.10, 127.63, 127.55, 126.96, 126.68, 126.39, 125.67, 123.92, 117.28, 98.50, 70.41, 69.91, 55.99, 53.37, 51.55, 37.60, 31.04, 26.25, 25.94, 25.64, 22.11.

STEP G: 5-{4-[(cyclohexylmethyl-amino)-methyl]-phenyl}-1-(2,4-dihydroxy-5-isopropyl-phenyl)-1H-[1,2,3]triazole-4-carboxylic acid ethylamide The title compound was obtained as a white solid after purification by column chromatography (DCM/MeOH:90/10).

Yield: 42% (37 mg).

$^1$H NMR (400 MHz, MeOP) δ: 7.35 (AB system, J=8.4 Hz, 4H), 6.88 (s, 1H), 6.31 (s, 1H), 3.86 (s, 2H), 3.39 (q, J=7.2 Hz, 2H), 3.15-3.05 (m, 1H), 2.52 (d, J=6.8 Hz, 2H), 1.78-1.50 (m, 6H), 1.27-1.24 (m, 3H), 1.21 (t, J=7.2 Hz, 3H), 1.08 (d, J=6.8 Hz, 6H), 0.99-0.87 (m, 2H).

$^{13}$C NMR (100 MHz, MeOD) δ: 161.04, 156.69, 150.95, 139.98, 137.54, 137.10, 129.75, 127.63, 126.27, 125.78, 125.04, 114.35, 101.90, 54.02, 51.69, 35.99, 33.24, 30.29, 25.57, 25.06, 21.15, 13.18.

Example 16

5-(4-cyclohexylaminomethyl-phenyl)-1-(2,4-dihydroxy-5-isopropyl-phenyl)-1H-[1,2,3]triazole-4-carboxylic acid ethylamide STEP E: 5-(4-cyclohexylaminomethyl-phenyl)-1-(2,4-dihydroxy-5-isopropyl-phenyl)-1H-[1,2,3]triazole-4-carboxylic acid methyl ester The title compound was obtained as an oil after purification by column chromatography (DCM/MeOH:95/5).

Yield: 30% (106 mg).

$^1$H NMR (400 MHz, CDCl$_3$) δ: 7.39-7.17 (m, 12H), 7.15 (s, 1H), 7.00-6.98 (m, 2H), 6.39 (s, 1H), 4.94 (s, 2H), 4.75 (s, 2H), 3.89 (s, 3H), 3.81 (s, 2H), 3.32-3.21 (m, 1H), 2.51-2.45 (m, 1H), 1.90 (d, J=12.0 Hz, 2H), 1.75-1.71 (m, 2H), 1.61 (d, J=10.4 Hz, 1H), 1.26-1.17 (m, 3H), 1.16-1.10 (m, 2H), 1.14 (d, J=6.8 Hz, 6H).

$^{13}$C NMR (100 MHz, CDCl$_3$) δ: 161.35, 157.42, 151.30, 142.58, 141.87, 135.97, 135.64, 135.03, 130.01, 129.49, 128.21, 128.10, 127.63, 127.56, 127.07, 126.69, 126.40, 125.68, 123.99, 117.26, 98.48, 70.41, 69.91, 56.00, 51.55, 50.19, 33.03, 25.94, 25.68, 24.54, 22.11.

STEP G: 5-(4-cyclohexylaminomethyl-phenyl)-1-(2,4-dihydroxy-5-isopropyl-phenyl)-1H-[1,2,3]triazole-4-carboxylic acid ethylamide The title compound was obtained as a white solid after purification by column chromatography (DCM/MeOH:90/10).

Yield: 40% (34 mg).

$^1$H NMR (400 MHz, MeOP) δ: 7.39 (AB system, J=8.4 Hz, 4H), 6.91 (s, 1H), 6.30 (s, 1H), 4.01 (s, 2H), 3.39 (q, J=7.2 Hz, 2H), 3.14-3.05 (m, 1H), 2.88-2.80 (m, 1H), 2.08-2.03 (m, 2H), 1.85-1.80 (m, 2H), 1.68 (d, J=12.0 Hz, 1H), 1.35-1.26 (m, 5H), 1.21 (t, J=7.2 Hz, 3H), 1.09 (d, J=6.8 Hz, 6H).

$^{13}$C NMR (100 MHz, MeOD) δ: 160.98, 156.76, 150.91, 139.88, 137.62, 135.19, 130.00, 127.93, 126.45, 126.29, 125.10, 114.30, 101.86, 56.20, 33.23, 29.69, 25.60, 24.63, 23.91, 21.13, 13.19.

Example 17

5-{4-[(2-diethylamino-ethylamino)-methyl]-phenyl}-1-(2,4-dihydroxy-5-isopropyl-phenyl)-1H-[1,2,3]triazole-4-carboxylic acid ethylamide STEP A: 1-(2,4-bis-benzyloxy-5-isopropyl-phenyl)-5-(4-bromomethyl-phenyl)-1H-[1,2,3]triazole-4-carboxylic acid methyl ester Triphenylphosphine (1.45 g, 5.54 mmol) and carbon tetrabromide (1.84 g, 5.54 mmol) were added to a solution of 1-(2,4-bis-benzyloxy-5-isopropyl-phenyl)-5-(4-hydroxymethyl-phenyl)-1H-[1,2,3]triazole-4-carboxylic acid methyl ester (2.4 g, 4.26 mmol) in dry DCM (48 ml) at 0° C. The mixture was stirred at this temperature for one hour, then the solvent was removed under reduced pressure and the residue was purified by column chromatography (PE/AcOEt: 70:30). The title compound was obtained as an oil (2.32 g, 87%).

Yield: 87% (2.32 g).

$^1$H NMR (400 MHz, CDCl$_3$) δ: 7.40-7.16 (m, 13H), 7.08-6.99 (m, 2H), 6.41 (s, 1H), 4.96 (s, 2H), 4.71 (s, 2H), 4.44 (s, 2H), 3.89 (s, 3H), 3.32-3.20 (m, 1H), 1.16 (d, J=6.8 Hz, 6H).

$^{13}$C NMR (100 MHz, CDCl$_3$) δ: 161.25, 157.50, 151.07, 141.84, 138.60, 135.93, 135.58, 135.18, 130.13, 129.79, 128.61, 128.13, 127.62, 126.69, 126.46, 125.68, 125.48, 117.00, 98.48, 70.40, 69.91, 51.59, 32.28, 26.00, 22.14.

STEP B: 1-(2,4-bis-benzyloxy-5-isopropyl-phenyl)-5-{4-[(2-diethylamino-ethylamino)-methyl]-phenyl}-1H-[1,2,3]triazole-4-carboxylic acid methyl ester N,N-diethylethylenediamine (0.6 mmol) was added at −10° C. to an acetonitrile solution of the bromide adduct obtained in Step A (125 mg, 0.2 mmol), and the reaction mixture was stirred for 30 minutes at this temperature and then warmed up to RT. After completion of the reaction (monitored by TLC), the solvent was removed under reduced pressure and the residue was purified by flash chromatography, the column being previously conditioned with ammonia (DCM/MeOH:80/10). The title compound was obtained as an oil (45%).

Yield: 45% (59 mg).

$^1$H NMR (400 MHz, CDCl$_3$) δ: 7.36-7.15 (m, 12H), 7.13 (s, 1H), 7.00-6.98 (m, 2H), 6.40 (s, 1H), 4.93 (s, 2H), 4.74 (s, 2H), 3.86 (s, 3H), 3.80 (s, 2H), 3.28-3.21 (m, 1H), 2.76 (t, J=6.0 Hz, 2H), 2.68 (t, J=6.0 Hz, 2H), 2.64 (q, J=7.2 Hz, 4H), 1.12 (d, J=6.8 Hz, 6H), 1.06 (t, J=7.2 Hz, 6H).

$^{13}$C NMR (100 MHz, CDCl$_3$) δ: 161.31, 157.45, 151.29, 142.50, 141.06, 135.96, 135.62, 135.04, 129.97, 129.49, 128.19, 128.08, 127.61, 127.56, 127.12, 126.69, 126.42, 125.58, 124.16, 117.15, 98.46, 70.39, 69.89, 52.97, 51.79, 51.52, 46.55, 45.61, 25.93, 22.09, 10.49.

STEP C: 5-{4-[(2-diethylamino-ethylamino)-methyl]-phenyl}-1-(2,4-dihydroxy-5-isopropyl-phenyl)-1H-[1,2,3]triazole-4-carboxylic acid ethylamide This compound has been synthesized following the procedure described in Steps F and G of examples 5-16. The title compound was obtained as a white solid after purification by column chromatography, the column being previously conditioned with ammonia (gradient DCM/MeOH:85/15 to 50/50).

Yield: 35% (16 mg).

$^1$H NMR (400 MHz, MeOD) δ: 7.31 (AB system, J=8.0 Hz, 4H), 6.84 (s, 1H), 6.29 (s, 1H), 3.73 (s, 2H), 3.38 (q, J=2H), 3.13-3.06 (m, 1H), 2.65-2.56 (m, 4H), 2.52 (q, J=7.2 Hz, 4H), 1.21 (t, J=7.2 Hz, 3H), 1.07 (d, J=7.2 Hz, 6H), 1.01 (t, J=7.2 Hz, 6H).

$^{13}$C NMR (100 MHz, MeOD) δ: 161.16, 156.71, 142.00, 140.06, 137.50, 129.59, 127.01, 125.76, 124.93, 114.57, 102.27, 52.22, 50.94, 46.25, 44.86, 33.25, 25.53, 21.20, 13.19, 9.69.

Examples 18-22 have been synthesized following the procedure as described in example 17 and using the adequate amine in Step B instead of N,N-diethylethylenediamine.

Example 18

5-{4-[(3-diethylamino-propylamino)-methyl]-phenyl}-1-(2,4-dihydroxy-5-isopropyl-phenyl)-1H-[1,2,3]triazole-4-carboxylic acid ethylamide The title compound was obtained as a white solid after purification by column chromatography, the column being previously conditioned with ammonia (gradient DCM/MeOH:90/10 to 20/20).

Yield: 32% (14 mg).

$^1$H NMR (400 MHz, MeOD) δ: 7.31 (AB system, J=8.0 Hz, 4H), 6.74 (s, 1H), 6.25 (s, 1H), 3.71 (s, 2H), 3.38 (q, J=7.2 Hz, 2H), 3.11-3.04 (m, 1H), 2.57-2.45 (m, 8H), 1.69-1.62 (m, 1H), 1.21 (t, J=7.2 Hz, 3H), 1.06-1.00 (m, 12H).

$^{13}$C NMR (100 MHz, MeOD) δ: 161.26, 156.86, 140.05, 139.95, 129.61, 127.04, 124.84, 124.72, 114.84, 102.90, 52.78, 52.22, 50.10, 45.81, 33.26, 25.44, 24.83, 21.28, 13.16, 9.41.

Example 19

1-(2,4-dihydroxy-5-isopropyl-phenyl)-5-{4-[(1-methyl-piperidin-4-ylamino)-methyl]-phenyl}-1H-[1,2,3]triazole-4-carboxylic acid ethylamide The title compound was obtained as a white solid after purification by column chromatography, the column being previously conditioned with ammonia (DCM/MeOH:1/1).

Yield: 35% (17 mg).

$^1$H NMR (400 MHz, MeOD) δ: 7.31 (AB system, J=8.4 Hz, 4H), 6.87 (s, 1H), 6.30 (s, 1H), 3.76 (s, 2H), 3.39 (q, J=7.2 Hz, 2H), 3.16-3.07 (m, 1H), 2.86-2.83 (m, 2H), 2.49-2.42 (m, 1H), 2.25 (s, 3H), 2.01 (t, J=11.2 Hz, 2H), 1.91-1.87 (m, 2H), 1.48-1.38 (m, 2H), 1.21 (t, J=7.2 Hz, 3H), 1.08 (d, J=6.8 Hz, 6H).

$^{13}$C NMR (100 MHz, MeOD) δ: 156.69, 150.84, 140.05, 137.88, 137.63, 129.79, 127.42, 126.33, 125.66, 125.12, 114.36, 101.84, 52.70, 52.11, 48.61, 43.31, 33.22, 28.85, 25.58, 21.13, 13.18.

Example 20

1-(2,4-dihydroxy-5-isopropyl-phenyl)-5-[4-((S)-3-dimethylamino-pyrrolidin-1-ylmethyl)-phenyl]-1H-[1,2,3]triazole-4-carboxylic acid ethylamide The title compound was obtained as a white solid after purification by column chromatography, the column being previously conditioned with ammonia (gradient DCM/MeOH:85/15 to 60/40).

Yield: 42% (22 mg).

$^1$H NMR (400 MHz, MeOD) δ: 7.29 (AB system, J=8.0 Hz, 6.84 (s, 1H), 6.33 (s, 1H), 3.59 (q, J=7.2 Hz, 2H), 3.39 (q, J=7.2 Hz, 2H), 3.13-3.07 (m, 1H), 2.94-2.78 (m, 2H), 2.71-2.65 (m, 1H), 2.56-2.50 (m, 1H), 2.36-2.32 (m, 1H), 2.26 (s, 6H), 2.09-1.97 (m, 1H), 1.78-1.67 (m, 1H), 1.21 (t, J=7.2 Hz, 3H), 1.07 (d, J=6.8 Hz, 6H).

$^{13}$C NMR (100 MHz, MeOD) δ: 161.09, 156.59, 150.87, 140.08, 138.87, 129.45, 127.66, 126.32, 125.01, 114.42, 101.91, 64.60, 59.04, 56.60, 52.25, 41.73, 33.24, 27.46, 25.50, 21.15, 13.18.

Example 21

1-(2,4-dihydroxy-5-isopropyl-phenyl)-5-(4-pyrrolidin-1-ylmethyl-phenyl)-1H-[1,2,3]triazole-4-carboxylic acid ethylamide The title compound was obtained as a white solid after purification by column chromatography (DCM/MeOH:85/15).

Yield: 68% (32 mg).

$^1$H NMR (400 MHz, MeOD) δ: 7.31 (AB system, J=8.0 Hz, 4H), 6.85 (s, 1H), 6.32 (s, 1H), 3.66 (s, 2H), 3.39 (q, J=7.2 Hz, 2H), 3.13-3.06 (m, 1H), 2.58-2.54 (m, 4H), 1.81-1.77 (m, 4H), 1.21 (t, J=7.2 Hz, 3H), 1.06 (d, J=6.8 Hz, 6H).

$^{13}$C NMR (100 MHz, MeOD) δ: 161.08, 156.62, 150.94, 140.02, 138.20, 137.46, 129.51, 128.06, 126.29, 125.29, 125.00, 114.42, 101.93, 59.01, 53.04, 33.25, 25.54, 22.19, 21.13, 13.19.

Example 22

1-(2,4-dihydroxy-5-isopropyl-phenyl)-5-(4-imidazol-1-ylmethyl-phenyl)-1H-[1,2,3]triazole-4-carboxylic acid ethylamide The title compound was obtained as a white solid after purification by column chromatography, the column being previously conditioned with ammonia (gradient DCM/MeOH:95/5 to 90/10).

Yield: 54% (25 mg).

$^1$H NMR (400 MHz, MeOD) δ: 7.71 (s, 1H), 7.25 (AX system, J=8.0 Hz, 4H), 7.06 (s, 1H), 6.96 (s, 1H), 6.88 (s, 1H), 6.32 (s, 1H), 5.17 (s, 2H), 3.37 (q, J=7.2 Hz, 2H), 3.14-3.05 (m, 1H), 1.20 (t, J=7.2 Hz, 3H), 1.06 (d, J=6.8 Hz, 6H).

$^{13}$C NMR (100 MHz, MeOD) δ: 161.00, 156.66, 150.69, 139.79, 137.57, 136.76, 129.99, 127.31, 126.46, 126.17, 125.97, 125.02, 119.23, 114.32, 101.93, 49.40, 33.26, 25.55, 21.16, 13.20.

Example 23

4-isopropyl-6-[5-(4-morpholin-4-yl-phenylamino)-[1,2,3]triazol-1-yl]-benzene-1,3-diol STEP A: bromoethynyl-triisopropyl-silane NBS (2.14 g, 12 mmol) and AgNO$_3$ (170 mg, 1 mmol) were added to a solution of triisopropylsilylacetylene (2.24 ml, 10 mmol) in acetone (15 ml). The solution was stirred for 2 hours at RT. Pentane (20 ml) and H$_2$O (20 ml) were added and the solution was stirred for 30 minutes. The organic phase was extracted with pentane (3×20 ml) and dried over Na$_2$SO$_4$. The solvent was removed under reduced pressure at RT and the residue was used in the next reaction without any purification.

STEP B: (4-morpholin-4-yl-phenyl)-[(triisopropylsilanyl)-ethynyl]-carbamic acid tert-butyl ester A suspension of t-butyl 4-morpholinophenylcarbamate (1.45 g, 7.60 mmol), bromoethynyl-triisopropyl-silane, CuI (450 mg, 2.34 mmol) and 1,10-phenanthroline (500 mg, 2.80 mmol) in dry toluene (15 ml) was warmed up to 90° C. under a nitrogen atmosphere. KHMDS (20 ml, 0.5 M in toluene) was added dropwise under nitrogen and the mixture was stirred for 12 hours at this temperature. The reaction was cooled down to RT; Et$_2$O (30 ml) and NaCl/NH$_4$OH (60/30 ml) were added and the organic phase was extracted with Et$_2$O (3×30 ml), washed with NaCl/NH$_4$ and dried over Na$_2$SO$_4$. The solvent was removed under reduced pressure and the title compound was obtained after purification by column chromatography (PE/AcOEt: 95/5).

Yield: 40% (1.83 g).

$^1$H NMR (400 MHz, CDCl$_3$) δ: 7.38 (d, J=8.8 Hz, 2H), 6.82 (d, J=8.8 Hz, 2H), 3.72 (t, J=4.6 Hz, 4H), 3.12 (t, J=4.6 Hz, 4H), 1.51 (s, 9H), 1.28-1.05 (m, 21H).

STEP C: ethynyl-(4-morpholin-4-yl-phenyl)-carbamic acid tert-butyl ester

TBAF (954 mg, 3.02 mmol) was added to a solution of (4-morpholin-4-yl-phenyl)-[(triisopropylsilanyl)-ethynyl]-carbamic acid tert-butyl ester (600 mg, 1.31 mmol) in THF (10 ml) at 0° C. The mixture was stirred for 1 hour at this temperature and was then warmed up to RT. H$_2$O (15 ml) was added and the organic phase was extracted with Et$_2$O (3×15 ml) and dried over Na$_2$SO$_4$. The solvent was removed under reduced pressure and the desired compound was obtained after purification by column chromatography (PE/AcOEt:80/20 to 75/25). The title compound was obtained as yellow solid.

Yield: 80% (313 mg).

$^1$H NMR (400 MHz, CDCl$_3$) δ: 7.27 (d, J=7.2 Hz, 2H), 6.83 (d, J=7.2 Hz, 2H), 3.79 (t, J=4.8 Hz, 4H), 3.09 (t, J=4.8 Hz, 4H), 2.81 (s, 1H), 1.48 (s, 9H).

STEP D: [3-(2,4-bis-benzyloxy-5-isopropyl-phenyl)-3H-[1,2,3]triazol-4-yl]-(4-morpholin-4-yl-phenyl)-carbamic acid tert-butyl ester A solution of 1,5-bis-benzyloxy-2-isopropyl-4-azido-benzene (373 mg, 1 mmol) and ethynyl-(4-morpholin-4-yl-phenyl)-carbamic acid t-butyl ester (275 mg, 0.91 mmol) in DMF (2.5 ml) was flushed with nitrogen three times as previously described before adding [Cp*Ru]4 (49 mg, 0.045 mmol) and repeating the three cycle-degassing with nitrogen. The reaction mixture was stirred at RT until completion (i.e., monitored by TLC). AcOEt and H$_2$O were then added. The organic phase was extracted four times with AcOEt, washed with water (three times) and brine (once) and dried over Na$_2$SO$_4$. The solvent was removed under reduced pressure and the reaction mixture was purified by column chromatography (PE/AcOEt:60/40). The title compound was obtained as an oil.

Yield: 62% (418 mg).

$^1$H NMR (400 MHz, CDCl$_3$) δ: 7.40-7.16 (m, 12H), 6.75 (AB system, J=8.2 Hz, 4H), 6.70 (s, 1H), 5.10 (s, 2H), 4.97 (s, 2H), 3.72 (t, J=4.8 Hz, 4H), 3.32 (quint, J=6.8 Hz, 1H), 3.05 (t, J=4.8 Hz, 4H), 1.28 (s, 9H), 1.23 (d, J=6.8 Hz, 6H).

STEP E: [3-(2,4-dihydroxy-5-isopropyl-phenyl)-3H-[1,2,3]triazol-4-yl]-(4-morpholin-4-yl-phenyl)-carbamic acid t-butyl ester Pd(OH)$_2$/C (0.02 mmol) was added to [3-(2,4-bis-benzyloxy-5-isopropyl-phenyl)-3H-[1,2,3]triazol-4-yl]-(4-morpholin-4-yl-phenyl)-carbamic acid t-butyl ester (135 mg, 0.2 mmol) dissolved in EtOH (5 ml) and the mixture was subjected to one atmosphere of H$_2$ for 1 hour. The catalyst was filtered off through Celite® pad and ethanol was removed under reduced pressure. The crude reaction mixture was used in the next reaction without any purification.

STEP F: 4-isopropyl-6-[5-(4-morpholin-4-yl-phenylamino)-[1,2,3]triazol-1-yl]-benzene-1,3-diol A solution of the intermediate from Step E in DCM/TFA (1/1 5 ml) was stirred for 12 hours at RT. The reaction mixture was concentrated under reduced pressure and the crude reaction mixture was purified by column chromatography (DCM/MeOH: 95/5). The title compound was obtained as slightly brown solid.

Yield: 45% (36 mg).

$^1$H NMR (400 MHz, MeOD) δ: 7.35 (s, 1H), 7.04 (s, 1H), 7.03-6.93 (m, 5H), 6.50 (s, 1H), 4.80 (bs, 3H), 3.81-3.78 (m, 4H), 3.21-2.98 (m, 5H), 1.16 (d, J=7.2 Hz, 6H).

$^{13}$C NMR (100 MHz, MeOD) δ: 156.67, 150.06, 145.26, 141.64, 135.83, 126.97, 124.79, 118.08, 117.64, 117.17, 113.27, 102.31, 65.96, 50.25, 25.83, 21.15.

Example 24

4-isopropyl-6-[5-(4-morpholin-4-yl-benzylamino)-[1,2,3]triazol-1-yl]-benzene-1,3-diol STEP A: (4-morpholin-4-yl-benzyl)-[(triisopropylsilanyl)-ethynyl]-carbamic acid t-butyl ester A suspension of t-butyl 4-morpholinobenzylcarbamate (1.11 g, 3.80 mmol), bromoethynyl-triisopropyl-silane, CuI (225 mg, 1.17 mmol) and 1,10-phenantroline (250 mg, 1.40 mmol) in dry toluene (7.5 ml) was warmed to 90° C. under a nitrogen atmosphere. KHMDS (10 ml, 0.5 M in toluene) was added dropwise under nitrogen atmosphere and the mixture was stirred for 12 hours at this temperature. The reaction mixture was cooled to RT; Et$_2$O (30 ml) and NaCl/NH$_4$OH (60/30 ml) were added and the organic phase was extracted with Et$_2$O (3×30 ml), washed with NaCl/NH$_4$ and dried over Na$_2$SO$_4$. The solvent was removed under reduced pressure to afford the title compound which was purified by column chromatography (PE/AcOEt:95/5).

Yield: 76% (1.37 g).

$^1$H NMR (400 MHz, CDCl$_3$) δ: 7.33 (d, J=8.8 Hz, 2H), 6.78 (d, J=8.8 Hz, 2H), 4.32 (s, 2H), 3.68 (t, J=4.6 Hz, 4H), 3.08 (t, J=4.6 Hz, 4H), 1.48 (s, 9H), 1.25-1.04 (m, 21H).

STEP B: ethynyl-(4-morpholin-4-yl-benzyl)-carbamic acid t-butyl ester

TBAF (2.18 g, 6.9 mmol) was added to a solution of (4-morpholin-4-yl-benzyl)-[(triisopropylsilanyl)-ethynyl]-carbamic acid t-butyl ester (1.42 g, 3 mmol) in THF (23 ml) at 0° C. The mixture was stirred for 1 hour at this temperature and was then warmed to RT. H$_2$O (15 ml) was added and the organic phase was extracted with Et$_2$O (3×15 ml) and dried over Na$_2$SO$_4$. The solvent was removed under reduced pressure and the desired compound was obtained after purification by column chromatography (PE/AcOEt:80/20 to 75/25). The title compound was obtained as a yellow solid.

Yield: 60% (570 mg).

$^1$H NMR (400 MHz, CDCl$_3$) δ: 7.24-7.33 (d, J=8.8 Hz, 2H), 6.84 (d, J=8.8 Hz, 2H), 4.57 (s, 2H), 3.84 (t, J=4.6 Hz, 4H), 3.37 (t, J=4.6 Hz, 4H), 2.48 (s, 1H), 1.43 (s, 9H).

STEP C: [3-(2,4-bis-benzyloxy-5-isopropyl-phenyl)-3H-[1,2,3]triazol-4-yl]-(4-morpholin-4-yl-benzyl)-carbamic acid tert-butyl ester A solution of 1,5-bis-benzyloxy-2-isopropyl-4-azido-benzene (240 mg, 0.64 mmol) and t-butyl ethynyl(4-morpholinobenzyl)carbamate (185 mg, 0.58 mmol) in DMF (2.5 ml) was degassed at RT by means of three vacuum-nitrogen cycles before adding [Cp*RuCl]4 (32 mg, 0.029 mmol). The reaction mixture was stirred at RT until completion (i.e., monitored by TLC). AcOEt and H$_2$O were then added. The organic phase was extracted four times with AcOEt, washed with water (three times) and brine (once) and dried over Na$_2$SO$_4$. The solvent was removed under reduced pressure and the reaction mixture was purified by column chromatography (PE/AcOEt:60/40). The title compound was obtained as an oil.

Yield: 56% (225 mg).

$^1$H NMR (400 MHz, CDCl$_3$) δ: 7.40-7.20 (m, 12H), 6.76 (AB system, J=8.4 Hz, 4H), 6.64 (s, 1H), 5.08 (s, 2H), 4.96 (s, 2H), 4.32-4.28 (m, 2H), 3.81 (t, J=4.8 Hz, 4H), 3.34 (quint, J=6.8 Hz, 1H), 3.08 (t, J=4.8 Hz, 4H), 1.27 (s, 9H), 1.22 (d, J=6.8 Hz, 6H).

STEP D: tert-butyl 1-(2,4-dihydroxy-5-isopropylphenyl)-1H-1,2,3-triazol-5-yl(4-morpholinobenzyl)carbamate A mixture of Pd(OH)$_2$/C (0.02 mmol), [3-(2,4-bis-benzyloxy-5-isopropyl-phenyl)-3H-[1,2,3]triazol-4-yl]-(4-morpholin-4-yl-benzyl)-carbamic acid t-butyl ester (138 mg, 0.2 mmol) in EtOH (5 ml) was subjected to one atmosphere of H$_2$ for 1 hour. The catalyst was filtered off through Celite® pad and ethanol was then removed under reduced pressure. The crude reaction mixture was used in the next reaction without any purification.

STEP E: 4-isopropyl-6-[5-(4-morpholin-4-yl-benzylamino)-[1,2,3]triazol-1-yl]-benzene-1,3-diol A solution of the intermediate from Step D in DCM/TFA (1/1, 5 ml) was stirred for 12 hours at RT. The reaction mixture was concentrated under reduced pressure and the crude reaction mixture was purified by column chromatography (DCM/MeOH: 95/5). The title compound was obtained as slightly brown solid.

Yield: 50% (41 mg).

$^1$H NMR (400 MHz, MeOD) δ: 7.19 (d, J=8.8 Hz, 2H), 6.98 (s, 1H), 6.86 (d, J=8.8 Hz, 2H), 6.85 (s, 1H), 6.50 (s, 1H), 4.85 (bs, 3H), 4.16 (s, 2H), 3.76-3.74 (m, 4H), 3.21-3.15 (m, 1H), 3.05-3.03 (m, 4H), 1.16 (d, J=6.0 Hz, 6H).

$^{13}$C NMR (100 MHz, MeOD) δ: 156.55, 150.29, 150.04, 145.45, 129.65, 127.46, 126.99, 124.77, 115.28, 114.10, 113.24, 102.34, 66.12, 48.99, 25.85, 21.19.

Example 25

1-(2,4-dihydroxy-5-isopropyl-phenyl)-5-(4-morpholin-4-yl-phenylamino)-1H-[1,2,3]triazole-4-carboxylic acid ethylamide STEP A: [tert-butoxycarbonyl-(4-morpholin-4-yl-phenyl)-amino]-propynoic acid methyl ester LiHMDS (4.35 ml, 1 M in THF, 4.35 mmol) was added to a solution of ethynyl-(4-morpholin-4-yl-phenyl)-carbamic acid tert-butyl ester (750 mg, 2.5 mmol, in dry THF (4.3 ml) under nitrogen at −78° C. The mixture was slowly warmed up to −40° C. and maintained at this temperature for 1 hour. The latter was then transferred dropwise via cannula to a solution of ClCO$_2$Me (314 μl, 4.06 mmol) in THF (7.5 ml) at −40° C. The resulting mixture was allowed to return to RT. Saturated aqueous NH$_4$Cl and AcOEt were added and the organic phase was extracted (3×15 ml AcOEt) and dried over Na$_2$SO$_4$. The title compound was obtained after purification by column chromatography (PE/AcOEt:80/20 to 75/25).

Yield: 61% (550 mg).

$^1$H NMR (400 MHz, CDCl$_3$) δ: 7.22 (d, J=8.8 Hz, 2H), 6.84 (d, J=8.8 Hz, 2H), 3.80 (t, J=4.8 Hz, 4H), 3.70 (s, 3H), 3.11 (t, J=4.8 Hz, 4H), 1.50 (s, 9H).

STEP B: 1-(2,4-bis-benzyloxy-5-isopropyl-phenyl)-5-[tert-butoxycarbonyl-(4-morpholin-4-yl-phenyl)-amino]-1H-[1,2,3]triazole-4-carboxylic acid methyl ester A solution of 1,5-bis-benzyloxy-2-isopropyl-4-azido-benzene (373 mg, 1 mmol) and [t-butoxycarbonyl-(4-morpholin-4-yl-phenyl)-amino]-propynoic acid methyl ester (328 mg, 0.91 mmol) in DMF (2.5 ml) was degassed at RT by means of three vacuum-nitrogen cycles before adding [Cp*RuCl]4 (49 mg, 0.045 mmol) and repeating the three degassing cycles with nitrogen. The reaction mixture was stirred at RT until completion (i.e., monitored by TLC). AcOEt and H$_2$O were then added. The organic phase was extracted four times with AcOEt, washed with water (three times) and brine (once) and dried over Na$_2$SO$_4$. The solvent was removed under reduced pressure and the reaction mixture was purified by column chromatography (PE/AcOEt:60/40). The title compound was obtained as an oil.

Yield: 70% (467 mg).

$^1$H NMR (400 MHz, CDCl$_3$) δ: 7.38-7.18 (m, 9H), 6.98-6.96 (m, 2H), 6.64 (d, J=8.8 Hz, 2H), 6.48 (d, J=8.8 Hz, 2H), 6.41 (s, 1H), 5.0 (s, 2H), 4.73-4.52 (m, 2H), 3.95 (s, 3H), 3.74 (t, J=4.4 Hz, 4H), 3.27-3.22 (m, 1H), 2.93-2.91 (m, 4H), 1.32 (s, 9H), 1.12-1.10 (m, 6H).

STEP C: [3-(2,4-bis-benzyloxy-5-isopropyl-phenyl)-5-ethylcarbamoyl-3H-[1,2,3]triazol-4-yl]-(4-morpholin-4-yl-phenyl)-carbamic acid tert-butyl ester EtNH$_2$ (1.5 ml of a solution 2 M in MeOH) was added to 1-(2,4-bis-benzyloxy-5-isopropyl-phenyl)-5-[tert-butoxycarbonyl-(4-morpholin-4-yl-phenyl)-amino]-1H-[1,2,3]triazole-4-carboxylic acid methyl ester (110 mg, 0.15 mmol) and the mixture was heated to 80° C. for 24 hours in a sealed tube. The solvent and the excess of amine were removed under reduced pressure and the residue was used in the next reaction without any purification.

STEP D: [3-(2,4-dihydroxy-5-isopropyl-phenyl)-5-ethylcarbamoyl-3H-[1,2,3]triazol-4-yl]-(4-morpholin-4-yl-phenyl)-carbamic acid tert-butyl ester Intermediate obtained from Step C was hydrogenated for 1 hour in EtOH (5 ml) in the presence of Pd(OH)$_2$/C (0.015 mmol). The catalyst was filtered off through Celite® pad and ethanol was removed under reduced pressure. The crude reaction mixture was used in the next reaction without any purification.

STEP E: 1-(2,4-dihydroxy-5-isopropyl-phenyl)-5-(4-morpholin-4-yl-phenylamino)-1H-[1,2,3]triazole-4-carboxylic acid ethylamide A solution of the intermediate from Step D in DCM/TFA (1/1, 2 ml) was stirred for 12 hours at RT. The reaction mixture was concentrated under reduced pressure and the crude reaction mixture was purified by column chromatography (DCM/MeOH: 95/5). The title compound was obtained as a slightly brown solid.

Yield: 45% (36 mg).

$^1$H NMR (400 MHz, MeOD) δ: 6.74 (d, J=8.8 Hz, 2H), 6.69 (s, 1H), 6.57 (d, J=8.8 Hz, 2H), 6.10 (s, H), 4.80 (bs, 4H), 3.74 (t, J=4.8 Hz, 4H), 3.40 (q, J=7.2 Hz, 2H), 3.00 (t, J=6.8 Hz, 1H), 2.93 (t, J=4.8 Hz, 4H), 1.21 (t, J=7.2 Hz, 3H), 1.05 (d, J=6.8 Hz, 6H).

$^{13}$C NMR (100 MHz, MeOD) δ: 162.68, 156.03, 150.04, 148.20, 143.32, 130.27, 126.00, 124.40, 123.94, 123.18, 115.40, 114.47, 101.79, 66.05, 49.43, 32.89, 25.57, 21.24, 13.44.

Example 26

1-(2,4-dihydroxy-5-isopropyl-phenyl)-5-(4-morpholin-4-yl-benzylamino)-1H-[1,2,3]triazole-4-carboxylic acid ethylamide STEP A: [tert-butoxycarbonyl-(4-morpholin-4-yl-benzyl)-amino]-propynoic acid methyl ester It has been synthesized following the procedure described at example 25-STEP A, using ethynyl-(4-morpholin-4-yl-benzyl)-carbamic acid tert-butyl ester instead of ethynyl-(4-morpholin-4-yl-phenyl)-carbamic acid tert-butyl ester.

Yield: 75% (702 mg).

¹H NMR (400 MHz, CDCl$_3$) δ: 7.23 (d, J=8.8 Hz, 2H), 6.83 (d, J=8.8 Hz, 2H), 4.49 (s, 2H), 3.82-3.77 (m, 4H), 3.69 (s, 3H), 3.13-3.08 (m, 4H), 1.46 (s, 9H).

STEP B: 1-(2,4-bis-benzyloxy-5-isopropyl-phenyl)-5-[tert-butoxycarbonyl-(4-morpholin-4-yl-benzyl)-amino]-1H-[1,2,3]triazole-4-carboxylic acid methyl ester It has been synthesized following the procedure described at example 23-STEP D, using [tert-butoxycarbonyl-(4-morpholin-4-yl-benzyl)-amino]-propynoic acid methyl ester instead of ethynyl-(4-morpholin-4-yl-phenyl)-carbamic acid tert-butyl ester.

Yield: 54% (404 mg).

¹H NMR (400 MHz, CDCl$_3$) δ: 7.40-7.13 (m, 10H), 7.03 (s, 1H), 6.72 (d, J=8.0 Hz, 2H), 6.56 (s, 1H), 6.47 (d, J=8.0 Hz, 2H), 5.06 (s, 2H), 4.92 (AB system, J=7.8 Hz, 2H), 4.65 (d, J=6.8 Hz, 1H), 3.97 (d, J=6.8 Hz, 1H), 3.74 (t, J=4.6 Hz, 4H), 3.64 (s, 3H), 3.33 (quint, J=6.8 Hz, 1H), 2.97 (t, J=4.6 Hz, 4H), 1.23 (s, 9H), 1.32-1.22 (m, 6H).

STEP C: 1-(2,4-dihydroxy-5-isopropyl-phenyl)-5-(4-morpholin-4-yl-benzylamino)-1H-[1,2,3]triazole-4-carboxylic acid ethylamide It has been synthesized following the procedure described at example 25-STEP D, Yield: 48% (35 mg).

¹H NMR (400 MHz, MeOD) δ: 6.90 (d, J=8.4 Hz, 2H), 6.80 (s, 1H), 6.79 (d, J=8.4 Hz, 2H), 4.80 (bs, 4H), 4.04 (s, 2H), 3.76 (t, J=4.8 Hz, 4H), 3.37 (q, J=7.2 Hz, 2H), 3.14 (quint, J=6.8 Hz, 1H), 3.04 (t, J=4.8 Hz, 4H), 1.19 (t, J=7.2 Hz, 3H), 1.10 (d, J=6.8 Hz, 6H).

¹³C NMR (100 MHz, MeOD) δ: 162.97, 156.95, 151.39, 150.25, 146.00, 129.73, 127.03, 126.76, 126.47, 125.22, 115.18, 114.25, 101.85, 66.11, 48.90, 45.57, 32.81, 25.72, 21.17, 13.44.

Examples 27-31 have been synthesized following the procedure as described in example 5 (i.e., Steps F-G) but starting from 1-(2,4-bis-benzyloxy-5-isopropyl-phenyl)-5-(4-morpholin-4-ylmethyl-phenyl)-1H-[1,2,3]triazole-4-carboxylic acid ethyl ester (NMR characterization given in preparation 1) instead of 1-(2,4-bis-benzyloxy-5-isopropyl-phenyl)-5-(4-morpholin-4-ylmethyl-phenyl)-1H-[1,2,3]triazole-4-carboxylic acid methyl ester and using the adequate amine in Step F instead of EtNH$_2$.

Example 27

1-(2,4-dihydroxy-5-isopropyl-phenyl)-5-(4-morpholin-4-ylmethyl-phenyl)-1H-[1,2,3]triazole-4-carboxylic acid hexylamide STEP F: 1-(2,4-bis-benzyloxy-5-isopropyl-phenyl)-5-(4-morpholin-4-ylmethyl-phenyl)-1H-[1,2,3]triazole-4-carboxylic acid hexylamide The desired was obtained after purification by column chromatography (Hexane/AcOEt:70/30).

Yield: 85% (19 mg).

STEP G: 1-(2,4-dihydroxy-5-isopropyl-phenyl)-5-(4-morpholin-4-ylmethyl-phenyl)-1H-[1,2,3]triazole-4-carboxylic acid hexylamide The desired was obtained after purification by column chromatography (DCM/MeOH:98/2).

Yield: 62% (8 mg). ¹H NMR (75 MHz, DMSO-d6) δ: 9.78 (bs, 1H), 9.70 (bs, 1H), 8.49 (t, J=5.9 Hz, 1H), 7.23 (d, J=8.5 Hz, 2H), 7.19 (d, J=8.5 Hz, 2H), 6.87 (s, 1H), 6.37 (s, 1H), 3.51-3.54 (m, 4H), 3.39 (s, 2H), 3.16-3.22 (m, 2H), 3.00 (hept, J=6.7 Hz, 1H), 2.29-2.30 (m, 4H), 1.45-1.48 (m, 2H), 1.22-1.25 (m, 6H), 1.01 (d, J=6.9 Hz, 6H), 0.84 (t, J=6.6 Hz, 3H).

m/z 544.8 [M+Na]⁺.

Example 28

1-(2,4-dihydroxy-5-isopropyl-phenyl)-5-(4-morpholin-4-ylmethyl-phenyl)-1H-[1,2,3]triazole-4-carboxylic acid cyclopentylamide STEP F: 1-(2,4-bis-benzyloxy-5-isopropyl-phenyl)-5-(4-morpholin-4-ylmethyl-phenyl)-1H-[1,2,3]triazole-4-carboxylic acid cyclopentylamide The desired was obtained after purification by column chromatography (Hexane/AcOEt:60/40).

Yield: 40% (20 mg).

STEP G: 1-(2,4-dihydroxy-5-isopropyl-phenyl)-5-(4-morpholin-4-ylmethyl-phenyl)-1H-[1,2,3]triazole-4-carboxylic acid cyclopentylamide The desired was obtained after purification by column chromatography (DCM/MeOH:96/4).

Yield: 73% (11 mg).

¹H NMR (75 MHz, DMSO-d6) δ: 9.69 (s, 1H), 9.66 (s, 1H), 8.28 (d, J=7.8 Hz, 1H), 7.23 (d, J=8.5 Hz, 2H), 7.20 (d, J=8.5 Hz, 2H), 6.87 (s, 1H), 6.37 (s, 1H), 4.10-4.22 (m, 1H), 3.52-3.55 (m, 4H), 3.41 (bs, 2H), 3.00 (hept, J=6.9 Hz, 1H), 2.30 (bs, 4H), 1.45-1.90 (m, 8H), 0.99 (d, J=6.9 Hz, 6H).

m/z 529.0 [M+Na]⁺.

Example 29

1-(2,4-dihydroxy-5-isopropyl-phenyl)-5-(4-morpholin-4-ylmethyl-phenyl)-1H-[1,2,3]triazole-4-carboxylic acid cyclohexylamide STEP F: 1-(2,4-bis-benzyloxy-5-isopropyl-phenyl)-5-(4-morpholin-4-ylmethyl-phenyl)-1H-[1,2,3]triazole-4-carboxylic acid cyclohexylamide The desired was obtained after purification by column chromatography (Hexane/AcOEt:60/40).

Yield: 40% (27 mg).

STEP G: 1-(2,4-dihydroxy-5-isopropyl-phenyl)-5-(4-morpholin-4-ylmethyl-phenyl)-1H-[1,2,3]triazole-4-carboxylic acid cyclohexylamide The desired was obtained after purification by column chromatography (DCM/MeOH:96/4).

Yield: 40% (17 mg).

¹H NMR (75 MHz, DMSO-d6) δ: 9.74 (bs, 1H), 9.69 (bs, 1H), 8.19 (d, J=8.6 Hz, 1H), 7.23 (d, J=8.4 Hz, 2H), 7.19 (d, J=8.4 Hz, 2H), 6.87 (s, 1H), 6.37 (s, 1H), 3.69 (bs, 1H), 3.51-3.54 (m, 4H), 3.39 (bs, 2H), 3.00 (hept, J=6.7 Hz, 1H), 2.28-2.30 (m, 4H), 1.54-1.75 (m, 5H), 1.18-1.41 (m, 5H), 0.99 (d, J=6.7 Hz, 6H).

m/z 521.3 [M+H]⁺.

Example 30

[1-(2,4-dihydroxy-5-isopropyl-phenyl)-5-(4-morpholin-4-ylmethyl-phenyl)-1H-[1,2,3]triazol-4-yl]-morpholin-4-yl-methanone STEP F: [1-(2,4-bis-benzyloxy-5-isopropyl-phenyl)-5-(4-morpholin-4-ylmethyl-phenyl)-1H-[1,2,3]triazol-4-yl]-morpholin-4-yl-methanone The desired was obtained after purification by column chromatography (Hexane/AcOEt:10/40).

Yield: 87% (66 mg).

STEP G: [1-(2,4-dihydroxy-5-isopropyl-phenyl)-5-(4-morpholin-4-ylmethyl-phenyl)-1H-[1,2,3]triazol-4-0]-morpholin-4-yl-methanone The desired was obtained after purification by column chromatography (AcOEt/MeOH:95/5).

Yield: 17% (8 mg).

$^1$H NMR (75 MHz, DMSO-d6) δ: 9.76 (bs, 2H), 7.26 (d, J=8.1 Hz, 2H), 7.17 (d, J=8.1 Hz, 2H), 6.99 (s, 1H), 6.40 (s, 1H), 3.51-3.54 (m, 8H), 3.41 (bs, 2H), 3.2-3.3 (bm, 4H), 3.04 (hept, J=6.9 Hz, 1H), 2.27-2.30 (m, 4H), 1.03 (d, J=6.9 Hz, 6H).

m/z 508.2 [M+H]$^+$.

Example 31

(S)-2-{[1-(2,4-dihydroxy-5-isopropyl-phenyl)-5-(4-morpholin-4-ylmethyl-phenyl)-1H-[1,2,3]triazole-4-carbonyl]-amino}-3-methyl-butyric acid STEP F: (S)-2-{[1-(2,4-bis-benzyloxy-5-isopropyl-phenyl)-5-(4-morpholin-4-ylmethyl-phenyl)-1H-[1,2,3]triazole-4-carbonyl]-amino}-3-methyl-butyric acid The desired was obtained after purification by column chromatography (DCM/MeOHt:96/4).

Yield: 73% (62 mg).

STEP G: (S)-2-{[1-(2,4-dihydroxy-5-isopropyl-phenyl)-5-(4-morpholin-4-ylmethyl-phenyl)-1H-[1,2,3]triazole-4-carbonyl]-amino}-3-methyl-butyric acid The desired adduct was obtained after purification by preparative HPLC using a gradient of a binary mixture of H$_2$O/CH$_3$CN further containing 0.1% TFA from 90/10 to 10/90.

$^1$H NMR (300 MHz, MeOD) δ: 7.44-7.51 (m, 4H), 7.46 (d, J=8.7 Hz, 2H), 6.97 (s, 1H), 6.31 (s, 1H), 4.49 (m, 1H), 4.33 (bs, 2H), 3.88 (bs, 4H) 3.27 (bs, 4H), 3.12 (hept., J=6.9 Hz, 1H), 2.31 (m, 1H), 1.10 (d, J=6.9 Hz, 6H), 1.04 (d, J=6.9 Hz, 6H).

m/z 538.2 [M+H]$^+$.

Preparation 1

1-(2,4-bis-benzyloxy-5-isopropyl-phenyl)-5-(4-morpholin-4-ylmethyl-phenyl)-1H-[1,2,3]triazole-4-carboxylic acid ethyl ester $^1$H NMR (300 MHz, CDCl$_3$) δ: 7.20-7.41 (m, 12H), 7.09 (s, 1H), 7.01-7.05 (m, 2H), 6.41 (s, 1H), 4.96 (s, 2H), 4.78 (s, 2H), 4.37 (q, J=7.17 Hz, 2H), 3.75 (bs, 4H), 3.59 (bs, 2H), 3.26 (hept, J=6.9 Hz, 1H), 2.50 (bs, 4H), 1.35 (t, J=7.17 Hz, 3H), 1.11 (d, J=7.01 Hz, 6H).

Comparison Example 32

1-(5-chloro-2,4-dihydroxy-phenyl)-5-(4-fluoro-phenyl)-1H-[1,2,3]triazole-4-carboxylic acid ethyl ester This compound was obtained following the procedure described in example 1 steps A-D, starting from 4-chloro resorcinol and using 1-ethynyl-4-fluoro-benzene instead of (4-ethynylphenyl)-methanol in step D.

Comparison Example 33

4-chloro-6-[5-(4-fluoro-phenyl)-[1,2,3]triazol-1-yl]-benzene-1,3-diol

This compound was obtained following the procedure described in example 5 steps A-B and G, and using (4-fluoro-phenyl)-propynoic acid ethyl ester instead of [4-(tert-butyl-dimethyl-silanyloxymethyl)-phenyl]-propynoic acid methyl ester in step B.

Biological Results

Example 34

Fluorescence Polarization (FP)

GM-BODIPY (PerkinElmer, CUSN60342000MG) was previously dissolved in DMSO to obtain 10 mM stock solutions and kept at −20° C. until use.

Hsp90 (Stressgen, SPP-776), was previously dissolved in assay buffer (HFB) to form 2.2 μM stock solutions and kept at −80° C. until use.

The compounds were previously dissolved in DMSO to obtain stock solutions and kept at −20° C. The day of experiment, the compounds were prepared by serial dilutions in assay buffer (HFB) containing 20 mM HEPES (K) pH 7.3, 50 mM KCl, 5 mM MgCl$_2$, 20 mM Na$_2$MoO4 and 0.01% NP40. Before each use, 0.1 mg/ml Bovine Gamma globulin and 2 mM DTT were freshly added.

Fluorescence Polarization (FP) was performed in Opti-Plate™-96F well plates (Perkin Elmer, Zaventem, Belgium) using a plate reader (Wallac Envision 2101 multilabel reader, Perkin Elmer, Zaventem, Belgium). To evaluate the binding affinity of the molecules, 50 μl of the GM-BODIPY solution (100 nM) were added to 125 nM of Hsp90 in the presence of 5 μl of the test compounds at increasing concentrations. The plate was mixed on a shaker at 4° C. for 4 hours, and the FP values in mP (millipolarization units) were recorded. The IC$_{50}$ values were calculated as the inhibitor concentration where 50% of the tracer is displaced; each data point is the result of the average of triplicate wells, and was determined from a plot using nonlinear least-squares analysis. Curve fitting was performed using Prism GraphPad software program (GraphPad software, Inc., San Diego, Calif.). Results are given in table 1.

TABLE 1

| Example | Hsp90 (IC$_{50}$ nM) |
|---|---|
| 1 | ++++ |
| 2 | ++++ |
| 3 | ++++ |
| 4 | ++++ |
| 5 | ++++ |
| 6 | ++++ |
| 7 | ++++ |
| 8 | ++++ |
| 9 | ++++ |
| 10 | ++++ |
| 11 | ++++ |
| 12 | ++++ |
| 13 | ++++ |
| 14 | ++++ |
| 15 | ++++ |
| 16 | ++++ |
| 17 | ++++ |
| 18 | ++++ |
| 19 | ++++ |
| 20 | ++++ |
| 21 | ++++ |
| 22 | ++++ |
| 23 | +++ |
| 24 | ++ |
| 25 | +++ |
| 26 | ++++ |
| 27 | ++++ |
| 28 | ++++ |

TABLE 1-continued

| Example | Hsp90 (IC$_{50}$ nM) |
|---|---|
| 29 | +++ |
| 30 | ++ |
| 31 | ++ |
| 32 | NA |
| 33 | NA |

++++: [IC$_{50}$] < 50 nM;
+++: 50 nM ≤ [IC$_{50}$] < 100 nM;
++: 100 ≤ [IC$_{50}$] < 500 nM;
NA: not active.

The various derivatives were found to be surprisingly very potent inhibitors of Hsp90 enzyme.

Cytotoxicity Assay

The antiproliferative activity of novel Hsp90 inhibitors was also evaluated on various cancerous cell lines by means of the sulphorodamine B test (i.e., NCI-H460 non-small cell lung carcinoma, A431 epidermoid, A2780 ovarian, MDA-MB436 triple-negative breast, U87MG glioblastoma, A498 renal, HCT116 colon, MeWo melanoma, MiaPaCa2 pancreas, HeLa cervix uteri, NB4 promyelocytic leukemia). NCI-H460, A431, MDA-MB436, A2780, A498, HeLa, NB4 tumour cells were grown in RPMI 1640 containing 10% fetal bovine serum (i.e., FBS from GIBCO), L-glutamine, and 50 µg/ml gentamycin sulfate.

HCT116 cells were cultured in McCoy's medium containing 10% FBS, L-glutamine, and 50 µg/ml gentamycin sulfate.

MiaPaCa2 cells were cultured in DMEM medium containing 10% FBS, L-glutamine, and 50 µg/ml gentamycin sulfate.

MeWo and U87-MG cells were cultured in Eagle's Minimum Essential Medium (i.e., EMEM) containing 10% FBS, L-glutamine, 1 mM sodium pyruvate, 0.1 mM non-essential amino acids, 1.5 g/l sodium bicarbonate, and 50 µg/ml gentamycin sulphate.

All cell lines were maintained in a 37° C. incubator with saturated humidity and an atmosphere containing 95% air and 5% CO2, and were sub-cultured every 2-3 days. Tumour cells were seeded in 96-well tissue culture plates at approximately 10% confluence and were allowed to attach and recover for 24 h.

Example 35

NCI-H460 Non-Small Cell Lung Carcinoma

Varying concentrations of the drugs were then added to each well to calculate their IC$_{50}$ value (the concentration which inhibits the 50% of cell survival). The plates were incubated at 37° C. for 72 h. At the end of the treatment, the plates were washed by remotion of the supernatant and addition of PBS 3 times. 200 µl PBS and 50 µl of cold 80% trichloroacetic acid (TCA) were added. The plates were incubated on ice for at least 1 h. TCA was removed, the plates were washed 3 times by immersion in distilled-water and dried on paper and at 40° C. for 5 mM. Then 200 µl of 0.4% sulphorodamine B in 1% acetic acid were added. The plates were incubated at room temperature for 30 min. Sulphorodamine B was removed, the plates were washed by immersion in 1% acetic acid for 3 times, then they were dried on paper and at 40° C. for 5 min. Then, 200 µl Tris 10 mM were added, the plates were kept under stirring for 20 min. The cell survival was determined as optical density by a Multiskan spectrofluorimeter at 540 nm. The amount of cells killed was calculated as the percentage decrease in sulphorodamine B binding compared with control cultures.

The IC$_{50}$ values were calculated with the "ALLFIT" program and are reported in table 2.

TABLE 2

| Example | NCI-H460 (IC$_{50}$ nM) |
|---|---|
| 1 | ++ |
| 2 | ++++ |
| 3 | ++ |
| 4 | + |
| 5 | ++++ |
| 6 | +++ |
| 7 | +++ |
| 8 | ++ |
| 9 | ++++ |
| 10 | ++++ |
| 11 | ++++ |
| 12 | ++ |
| 13 | ++ |
| 14 | ++ |
| 15 | ++++ |
| 16 | ++++ |
| 17 | ++ |
| 18 | + |
| 20 | ++++ |
| 25 | + |
| 26 | ++ |
| 27 | ++++ |
| 28 | ++++ |
| 29 | ++++ |
| 32 | NA |
| 33 | NA |

++++: [IC$_{50}$] < 50 nM;
+++: 50 nM ≤ [IC$_{50}$] < 100 nM;
++: 100 ≤ [IC$_{50}$] < 500 nM;
+: 500 ≤ [IC$_{50}$] < 1000 nM;
NA: not active.

The various derivatives were found to be endowed with a potent cytotoxic activity against NCI-H460 NSCLC contrarily to counter-examples 32 and 33 which were totally deprived of any interesting biological activity.

Example 36

The other cell lines were screened against one single concentration of the various inhibitors (i.e., 500 nM), all experiments being made in octuplicate, following the protocol described at example 35. Since NB4 cell line was grown in suspension, a further step of centrifugation (i.e., 1600 g for 10 min) was added after the 72 hour incubation period.

It was surprisingly found that most of the compounds of the present invention presented a percentage of inhibition much higher than 50% on a large variety of cell lines, meanwhile comparison examples 32 and 33 proved to be completely inactive. The results are depicted in table 3 underneath.

TABLE 3

| Example | A431 | A2780 | MDA MB436 | U87MG | A498 | HCT116 | MeWo | MiaPaCa2 | HeLa | NB4 |
|---|---|---|---|---|---|---|---|---|---|---|
| 2 | ++ | ++ | ++ | + | + | ++ | ++ | ++ | ++ | ++ |
| 3 | ++ | ++ | ++ | NT | + | ++ | ++ | ++ | ++ | ++ |

TABLE 3-continued

| Example | A431 | A2780 | MDA MB436 | U87MG | A498 | HCT116 | MeWo | MiaPaCa2 | HeLa | NB4 |
|---|---|---|---|---|---|---|---|---|---|---|
| 5 | ++ | ++ | ++ | ++ | ++ | ++ | ++ | ++ | ++ | ++ |
| 6 | ++ | ++ | ++ | ++ | ++ | ++ | ++ | ++ | ++ | ++ |
| 7 | ++ | ++ | ++ | ++ | ++ | ++ | ++ | ++ | ++ | ++ |
| 8 | ++ | ++ | ++ | ++ | + | ++ | ++ | ++ | ++ | ++ |
| 9 | ++ | ++ | ++ | ++ | ++ | ++ | ++ | ++ | ++ | ++ |
| 11 | ++ | ++ | ++ | ++ | ++ | ++ | ++ | ++ | ++ | ++ |
| 12 | NT | ++ | ++ | NT | + | NT | NT | ++ | NT | NT |
| 13 | ++ | ++ | ++ | ++ | + | ++ | ++ | ++ | + | NT |
| 14 | ++ | ++ | ++ | ++ | NT | + | ++ | ++ | NT | NT |
| 15 | ++ | ++ | ++ | ++ | ++ | ++ | ++ | ++ | ++ | ++ |
| 17 | ++ | ++ | ++ | ++ | + | + | ++ | ++ | + | ++ |
| 20 | ++ | ++ | ++ | ++ | + | ++ | ++ | ++ | ++ | ++ |
| 21 | ++ | ++ | ++ | ++ | ++ | ++ | ++ | ++ | ++ | ++ |
| 22 | ++ | ++ | ++ | ++ | ++ | ++ | ++ | ++ | ++ | ++ |
| 26 | NT | ++ | NT | NT | ++ | ++ | + | ++ | NT | + |
| 27 | ++ | ++ | ++ | ++ | ++ | ++ | ++ | ++ | ++ | ++ |
| 28 | ++ | ++ | ++ | ++ | ++ | ++ | ++ | ++ | ++ | ++ |
| 29 | ++ | ++ | ++ | ++ | ++ | ++ | ++ | ++ | ++ | ++ |
| 32 | NA | NA | NA | NA | NA | NA | NA | NA | NA | + |
| 33 | NA | NA | NA | NA | NA | NA | NA | NA | NA | NA |

[++]: % inhibition ≥ 50%;
[+]: 50% ≥ % inhibition ≥ 30%;
NA: not active;
NT: not tested

The invention claimed is:

1. A compound of formula I

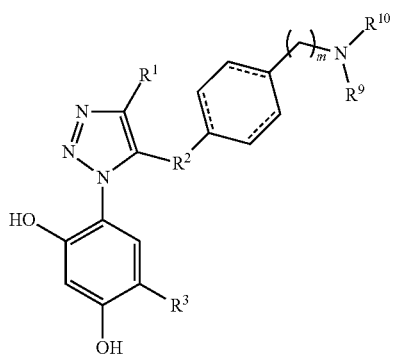

Formula I wherein, $R^1$ is H, $CONR^4R^5$;

$R^5$ is H, $(C_1-C_6)$-alkyl or $(C_3-C_{10})$-cycloalkyl each being optionally substituted once or more with OH, OMe, Cl, F;

$R^4$ is H, $(C_1-C_4)$-alkyl or $CH(R^{11})COR^{12}$; or $R^4$ and $R^5$ taken together with the nitrogen atom to which they are attached form a three to seven membered heterocycle optionally containing a further heteroatom selected from the group consisting of N, O or S; and wherein said heterocycle is optionally substituted once or more by OH, OMe, $(C_1-C_4)$-alkyl, optionally substituted phenyl, or benzyl;

$R^{11}$ is a side chain of a natural α-amino acid;

$R^{12}$ is OH, amino, alkylamino or dialkylamino;

$R^2$ is a bond, —NH(CO)—, —N($R^7$)— or —N($R^7$)CH$_2$—;

$R^7$ is H, $(C_1-C_4)$-alkyl or $CO_2R^8$;

$R^8$ is $(C_1-C_4)$-alkyl or benzyl;

the endocyclic symbols ⁓ are, for each single compound, all double bonds or all single bonds;

m is an integer comprised between 0 and 3;

$R^9$ and $R^{11}$ are independently from each other $(C_1-C_4)$-alkyl optionally substituted with OH, cycloalkyl, heterocycloalkyl, OMe, amino, $(C_1-C_6)$-alkylamino or $(C_1-C_6)$-dialkylamino;

heterocycloalkyl optionally substituted once or more by alkyl, amino, $(C_1-C_6)$-alkylamino or $(C_1-C_6)$-dialkylamino; cycloalkyl; or $R^9$ and $R^{10}$ taken together with the nitrogen atom to which they are attached form a heterocycle ring chosen from the group consisting of piperidyl, pyrrolidinyl, piperazinyl or morpholinyl, each of them being optionally substituted once or more by F, Cl, Br, OH, OMe, amino, $(C_1-C_6)$-alkylamino, $(C_1-C_6)$-dialkylamino, $(C_1-C_4)$-alkyl, hydroxyalkyl, optionally substituted phenyl, or benzyl; or an imidazole unsaturated heterocycle;

$R^3$ is Cl, Et or i-Pr;

or a tautomer, a geometrical isomer, an optically active form and a pharmaceutically acceptable salt thereof.

2. The compound of claim 1, wherein $R^1$ is $CONR^4R^5$.

3. The compound of claim 1 selected from the group consisting of 4-isopropyl-6-[5-(4-(morpholin-4-ylmethyl-phenyl)-[1,2,3]-triazol-1-yl)benzene-1,3-diol; 4-{5-[4-(3-hydroxy-piperidin-1-ylmethyl)-phenyl]-[1,2,3]triazol-1-yl}-6-isopropyl-benzene-1,3-diol; 4-{5-[4-(4-benzyl-piperazin-1-ylmethyl)-phenyl]-[1,2,3]triazol-1-yl}-6-isopropyl-benzene-1,3-diol; 4-isopropyl-6-{5-[4-(4-phenyl-piperazin-1-ylmethyl)-phenyl]-[1,2,3]triazol-1-yl}-benzene-1,3-diol; 1-(2,4-dihydroxy-5-isopropyl-phenyl)-5-(4-morpholin-4-ylmethyl-phenyl)-1H-[1,2,3]triazole-4-carboxylic ethyl amide; (R,S)-1-(2,4-dihydroxy-5-isopropyl-phenyl)-5-[4-(3-hydroxy-piperidin-1-ylmethyl)-phenyl]-1H-[1,2,3]triazole-4-carboxylic acid ethylamide; 1-(2,4-dihydroxy-5-isopropyl-phenyl)-5-(4-{[ethyl-(2-hydroxy-ethyl)-amino]-methyl}-phenyl)-1H-[1,2,3]triazole-4-carboxylic acid ethylamide; 1-(2,4-dihydroxy-5-isopropyl-phenyl)-5-{4-[2-(2-hydroxy-ethyl)-piperidin-1-ylmethyl]-phenyl}-1H-[1,2,3]triazole-4-carboxylic acid ethylamide; 1-(2,4-dihydroxy-5-isopropyl-phenyl)-5-(4-piperidin-1-ylmethyl-phenyl)-1H-[1,2,3]triazole-4-carboxylic acid ethylamide; 5-(4-diethylaminomethyl-phenyl)-1-(2,4-dihydroxy-5-isopropyl-phenyl)-1 H-[1,2,3]triazole-4-carboxylic acid ethylamide;

1-(2,4-dihydroxy-5-isopropyl-phenyl)-5-[4-(4-methyl-piperazin-1-ylmethyl)-phenyl]-1H-[1,2,3]triazole-4-carboxylic acid ethylamide; 1-(2,4-dihydroxy-5-isopropyl-phenyl)-5-(4-piperazin-1-ylmethyl-phenyl)-1H-[1,2,3]triazole-4-carboxylic acid ethylamide; 1-(2,4-dihydroxy-5-isopropyl-phenyl)-5-[4-(4-dimethylamino-piperidin-1-ylmethyl)-phenyl]-1H-[1,2,3]triazole-4-carboxylic acid ethylamide; 1-(2,4-dihydroxy-5-isopropyl-phenyl)-5-{4-[(2-morpholin-4-yl-ethylamino)-methyl]-phenyl}-1H-[1,2,3]triazole-4-carboxylic acid ethylamide; 5-{4-[(cyclohexylmethyl-amino)-methyl]-phenyl}-1-(2,4-dihydroxy-5-isopropyl-phenyl)-1H-[1,2,3]triazole-4-carboxylic acid ethylamide; 5-(4-cyclohexylaminomethyl-phenyl)-1-(2,4-dihydroxy-5-isopropyl-phenyl)-1H-[1,2,3]triazole-4-carboxylic acid ethylamide; 5-{4-[(2-Diethylamino-ethylamino)-methyl]-phenyl}-1-(2,4-dihydroxy-5-isopropyl-phenyl)-1H-[1,2,3]triazole-4-carboxylic acid ethylamide; 5-{4-[(3-diethyl-lamino-propylamino)-methyl]-phenyl}-1-(2,4-dihydroxy-5-isopropyl-phenyl)-1H-[1,2,3]triazole-4-carboxylic acid ethylamide; 1-(2,4-dihydroxy-5-isopropyl-phenyl)-5-{4-[(1-methyl-piperidin-4-ylamino)-methyl]-phenyl}-1H-[1,2,3]triazole-4-carboxylic acid ethylamide; 1-(2,4-dihydroxy-5-isopropyl-phenyl)-5-[4-((S)-3-dimethylamino-pyrrolidin-1-ylmethyl)-phenyl]-1H-[1,2,3]triazole-4-carboxylic acid ethylamide; 1-(2,4-dihydroxy-5-isopropyl-phenyl)-5-(4-pyrrolidin-1-ylmethyl-phenyl)-1H-[1,2,3]triazole-4-carboxylic acid ethylamide; 1-(2,4-dihydroxy-5-isopropyl-phenyl)-5-(4-imidazol-1-ylmethyl-phenyl)-1H-[1,2,3]triazole-4-carboxylic acid ethylamide; 4-isopropyl-6-[5-(4-morpholin-4-yl-phenylamino)-[1,2,3]triazol-1-yl]-benzene-1,3-diol; 4-isopropyl-6-[5-(4-morpholin-4-yl-benzylamino)-[1,2,3]triazol-1-yl]-benzene-1,3-diol; 1-(2,4-dihydroxy-5-isopropyl-phenyl)-5-(4-morpholin-4-yl-phenylamino)-1H-[1,2,3]triazole-4-carboxylic acid ethylamide; 1-(2,4-dihydroxy-5-isopropyl-phenyl)-5-(4-morpholin-4-yl-b enzylamino)-1H-[1,2,3]triazole-4-carboxylic acid ethylamide; 1-(2,4-dihydroxy-5-isopropyl-phenyl)-5-(4-morpholin-4-ylmethyl-phenyl)-1H-[1,2,3]triazole-4-carboxylic acid hexylamide; 1-(2,4-dihydroxy-5-isopropyl-phenyl)-5-(4-morpholin-4-yl-methyl-phenyl)-1H-[1,2,3]triazole-4-carboxylic acid cyclopentylamide; 1-(2,4-dihydroxy-5-isopropyl-phenyl)-5-(4-morpholin-4-ylmethyl-phenyl)-1H-[1,2,3]triazole-4-carboxylic acid cyclohexylamide; [1-(2,4-dihydroxy-5-isopropyl-phenyl)-5-(4-morpholin-4-ylmethyl-phenyl)-1H-[1,2,3]triazol-4-yl]-morpholin-4-yl-methanone; (S)-2-{[1-(2,4-dihydroxy-5-isopropyl-phenyl)-5-(4-morpholin-4-ylmethyl-phenyl)-1H-[1,2,3]triazole-4-carbonyl]-amino}-3-methyl-butyric acid; 4-isopropyl-6-[5-(4-pyrrolidin-1-ylmethyl-phenyl)-[1,2,3]triazol-1-yl]-benzene-1,3-diol; 4-isopropyl-6-[5-(4-isoxazolidin-2-ylmethyl-phenyl)-[1,2,3]triazol-1-yl]-benzene-1,3-diol; 1-(2,4-dihydroxy-5-isopropyl-phenyl)-5-(4-isoxazolidin-2-ylmethyl-phenyl)-1H-[1,2,3]triazole-4-carboxylic acid ethylamide; 1-(2,4-dihydroxy-5-isopropyl-phenyl)-5-[4-(4-phenyl-piperazin-1-ylmethyl)-phenyl]-1H-[1,2,3]triazole-4-carboxylic acid ethylamide; 4-[5-(4-{[Ethyl-(2-hydroxy-ethyl)-amino]-methyl}-phenyl)-[1,2,3]triazol-1-yl]-6-isopropyl-benzene-1,3-diol; 4-(5-{4-[2-(2-Hydroxy-ethyl)-piperidin-1-ylmethyl]-phenyl}-[1,2,3]triazol-1-yl)-6-isopropyl-benzene-1,3-diol; 4-isopropyl-6-[5-(4-piperidin-1-ylmethyl-phenyl)-[1,2,3]triazol-1-yl]-benzene-1,3-diol; 4-[5-(4-diethylaminomethyl-phenyl)-[1,2,3]triazol-1-yl]-6-isopropyl-benzene-1,3-diol; N-[3-(2,4-dihydroxy-5-isopropyl-phenyl)-3H-[1,2,3]triazol-4-yl]-4-morpholin-4-yl-benzamide; 1-(2,4-dihydroxy-5-isopropyl-phenyl)-5-(4-morpholin-4-yl-benzoylamino)-1H-[1,2,3]triazole-4-carboxylic acid ethylamide; N-[3-(2,4-dihydroxy-5-isopropyl-phenyl)-3H-[1,2,3]triazol-4-yl]-4-piperidin-1-yl-benzamide; 1-(2,4-dihydroxy-5-isopropyl-phenyl)-5-(4-piperidin-1-yl-benzoylamino)-1H-[1,2,3]triazole-4-carboxylic acid ethylamide; N-[3-(2,4-dihydroxy-5-isopropyl-phenyl)-3H-[1,2,3]triazol-4-yl]-4-(3-hydroxy-piperidin-1-yl)-benzamide; 1-(2,4-dihydroxy-5-isopropyl-phenyl)-5-[4-(3-hydroxy-piperidin-1-yl)-benzoylamino]-1H-[1,2,3]triazole-4-carboxylic acid ethylamide; N-[3-(2,4-dihydroxy-5-isopropyl-phenyl)-3H-[1,2,3]triazol-4-yl]-4-morpholin-4-ylmethyl-benzamide; 1-(2,4-dihydroxy-5-isopropyl-phenyl)-5-(4-morpholin-4-ylmethyl-benzoylamino)-1H-[1,2,3]triazole-4-carboxylic acid ethylamide; 4-morpholin-4-ylmethyl-cyclohexanecarboxylic acid [3-(2,4-dihydroxy-5-isopropyl-phenyl)-3H-[1,2,3]triazol-4-yl]-amide; 1-(2,4-dihydroxy-5-isopropyl-phenyl)-5-[(4-morpholin-4-ylmethyl-cyclohexanecarbonyl)-amino]-1H-[1,2,3]triazole-4-carboxylic acid ethylamide; 4-isopropyl-6-{5-[4-(4-methyl-piperazin-1-ylmethyl)-phenyl]-[1,2,3]triazol-1-yl}-benzene-1,3-diol; 4-isopropyl-6-[5-(4-morpholin-4-ylmethyl-phenyl)-[1,2,3]triazol-1-yl]-benzene-1,3-diol; 1-(2,4-dihydroxy-5-isopropyl-phenyl)-5-(4-morpholin-4-ylmethyl-phenyl)-1H-[1,2,3]triazole-4-carboxylic acid ethylamide; 5-[4-(4-benzyl-piperazin-1-ylmethyl)-phenyl]-1-(2,4-dihydroxy-5-isopropyl-phenyl)-1H-[1,2,3]triazole-4-carboxylic acid ethylamide; N-[3-(2,4-dihydroxy-5-isopropyl-phenyl)-3H-[1,2,3]triazol-4-yl]-4-pyrrolidin-1-yl-benzamide; 1-(2,4-dihydroxy-5-isopropyl-phenyl)-5-(4-pyrrolidin-1-yl-benzoylamino)-1H-[1,2,3]triazole-4-carboxylic acid ethylamide and 1-(2,4-dihydroxy-5-isopropyl-phenyl)-5-(4-morpholin-4-ylmethyl-phenyl)-1H-[1,2,3]triazole-4-carboxylic acid (2-chloro-ethyl)-amide.

4. A method of treating a pathological state for which the modulation of Hsp90 activity would result at improving the health of the patient, comprising administering a therapeutically effective amount of a compound of claim 1 to a patient in need thereof,
wherein the pathological state is a non-small cell lung carcinoma, epidermoid carcinoma, ovarian cancer, breast cancer, glioblastoma, renal cancer, colon cancer, melanoma, pancreas cancer, cervix uteri cancer, or promyelocytic leukemia.

5. A pharmaceutical composition containing at least one compound according to claim 1 as the active ingredient in mixtures with at least one pharmaceutically acceptable vehicle and/or excipient.

6. A process for synthesizing compounds of formula I

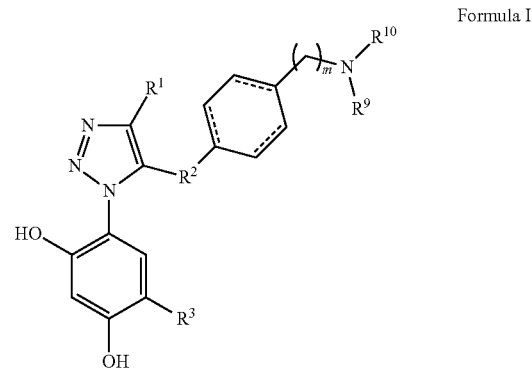

Formula I wherein $R^1$ is —$CONR^4R^5$;
$R^2$ is a bond;
m=1;

R⁵ is H, (C₁-C₆)-alkyl or (C₃-C₁₀)-cycloalkyl each being optionally substituted once or more with OH, OMe, Cl, F;

R⁴ is H, (C₁-C₄)-alkyl or CH(R¹¹)COR¹²; or

R⁴ and R⁵ taken together with the nitrogen atom to which they are attached form a three to seven membered heterocycle optionally containing a further heteroatom selected from the group consisting of N, O or S; and wherein said heterocycle is optionally substituted once or more by OH, OMe, (C₁-C₄)-alkyl, optionally substituted phenyl, or benzyl;

R¹¹ is a side chain of a natural α-amino acid;

R¹² is OH, amino, alkylamino or dialkylamino;

the endocyclic symbols ⁝⁝⁝ are, for each single compound, all double bonds or all single bonds;

R⁹ and R¹⁰ are independently from each other (C₁-C₄)-alkyl optionally substituted with OH, cycloalkyl, heterocycloalkyl, OMe, amino, (C₁-C₆)-alkylamino or (C₁-C₆)-dialkylamino;

heterocycloalkyl optionally substituted once or more by alkyl, amino, (C₁-C₆)-alkylamino or (C₁-C₆)-dialkylamino; cycloalkyl; or R⁹ and R¹⁰ taken together with the nitrogen atom to which they are attached form a heterocycle ring chosen from the group consisting of piperidyl, pyrrolidinyl, piperazinyl or morpholinyl, each of them being optionally substituted once or more by F, Cl, Br, OH, OMe, amino, (C₁-C₆)-alkylamino, (C₁-C₆)-dialkylamino, (C₁-C₄)-alkyl, hydroxyalkyl, optionally substituted phenyl, or benzyl; or an imidazole unsaturated heterocycle;

R³ is Cl, Et or i-Pr, the process comprising reacting a compound of formula II

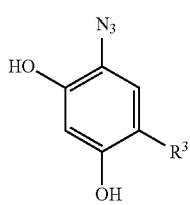

Formula II wherein R³ is Cl, Et or i-Pr, with a compound of formula III

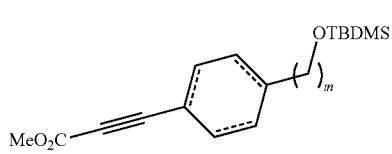

Formula III in a polar aprotic solvent in neutral atmosphere and in the presence of a ruthenium-based catalyst.

7. A process for synthesizing compounds of formula I

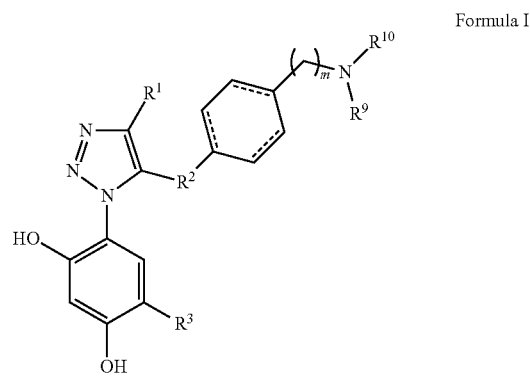

Formula I wherein R¹ is CONR⁴R⁵;

R² is —N(R⁷)— or —N(R⁷)CH₂—;

R⁵ is H, (C₁-C₆)-alkyl or (C₃-C₁₀)-cycloalkyl each being optionally substituted once or more with OH, OMe, Cl, F;

R⁴ is H, (C₁-C₄)-alkyl or CH(R¹¹)COR¹²; or

R⁴ and R⁵ taken together with the nitrogen atom to which they are attached form a three to seven membered heterocycle optionally containing a further heteroatom selected from the group consisting of N, O or S; and wherein said heterocycle is optionally substituted once or more by OH, OMe, (C₁-C₄)-alkyl, optionally substituted phenyl, or benzyl;

R¹¹ is a side chain of a natural α-amino acid;

R¹² is OH, amino, alkylamino or dialkylamino;

R⁷ is H, (C₁-C₄)-alkyl or CO₂R⁸;

R⁸ is (C₁-C₄)-alkyl or benzyl;

the endocyclic symbols ⁝⁝⁝ are, for each single compound, all double bonds or all single bonds;

m is an integer comprised between 0 and 3;

R⁹ and R¹⁰ are independently from each other (C₁-C₄)-alkyl optionally substituted with OH, cycloalkyl, heterocycloalkyl, OMe, amino, (C₁-C₆)-alkylamino or (C₁-C₆)-dialkylamino;

heterocycloalkyl optionally substituted once or more by alkyl, amino, (C₁-C₆)-alkylamino or (C₁-C₆)-dialkylamino; cycloalkyl; or R⁹ and R¹⁰ taken together with the nitrogen atom to which they are attached form a heterocycle ring chosen from the group consisting of piperidyl, pyrrolidinyl, piperazinyl or morpholinyl, each of them being optionally substituted once or more by F, Cl, Br, OH, OMe, amino, (C₁-C₆)-alkylamino, (C₁-C₆)-dialkylamino, (C₁-C₄)-alkyl, hydroxyalkyl, optionally substituted phenyl, or benzyl; or an imidazole unsaturated heterocycle;

R³ is Cl, Et or i-Pr, the process comprising reacting a compound of Formula II

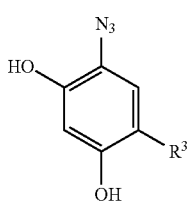

Formula II wherein R³ is Cl, Et or i-Pr with a compound of formula IV

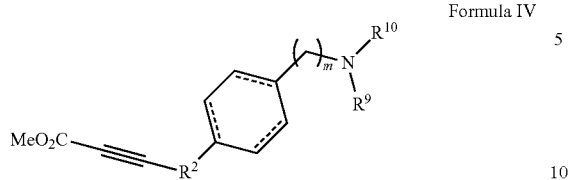

wherein R⁹ and R¹⁰ have the meaning defined above and R² is —N(R⁷)— or —N(R⁷)CH₂—, in a polar aprotic solvent in neutral atmosphere and in the presence of a ruthenium-based catalyst.

8. A process for preparing the pharmaceutical composition, comprising admixing at least one compound according to claim 1 with at least one pharmaceutically acceptable vehicle and/or excipient.

* * * * *